US011529107B2

(12) United States Patent
Dearing et al.

(10) Patent No.: US 11,529,107 B2
(45) Date of Patent: Dec. 20, 2022

(54) METHODS FOR AUTOMATIC GENERATION OF EEG MONTAGES

(71) Applicant: Cadwell Laboratories, Inc., Kennewick, WA (US)

(72) Inventors: Wayne Dearing, Kennewick, WA (US); Michael Schulz, Hermiston, OR (US); Alison Hull, Burbank, WA (US); Wes Hatley, West Richland, WA (US)

(73) Assignee: Cadwell Laboratories, Inc., Kennewick, WA (US)

( * ) Notice: Subject to any disclaimer, the term of this patent is extended or adjusted under 35 U.S.C. 154(b) by 265 days.

(21) Appl. No.: 16/697,850

(22) Filed: Nov. 27, 2019

(65) Prior Publication Data

US 2020/0163629 A1 May 28, 2020

Related U.S. Application Data

(60) Provisional application No. 62/771,897, filed on Nov. 27, 2018.

(51) Int. Cl.
*A61B 5/291* (2021.01)
*A61B 5/00* (2006.01)

(52) U.S. Cl.
CPC ............ *A61B 5/7435* (2013.01); *A61B 5/291* (2021.01); *A61B 5/743* (2013.01); *A61B 5/6868* (2013.01); *A61B 2562/04* (2013.01)

(58) Field of Classification Search
CPC ..... A61B 5/7475; A61B 5/742; A61B 5/7465; A61B 2562/04; A61B 5/0042;
(Continued)

(56) References Cited

U.S. PATENT DOCUMENTS 751,475 A 2/1904 De Vilbiss
2,320,709 A 6/1943 Arnesen
(Continued)

FOREIGN PATENT DOCUMENTS

CN 104766176 A 7/2015
DE 102014008684 A1 1/2016
(Continued)

OTHER PUBLICATIONS

Brainstorm Website, http://neuroimage.usc.edu/brainstorm/ accessed online Oct. 9, 2021, available online Apr. 11, 2018. (Year: 2018).*
(Continued)

*Primary Examiner* — Navin Natnithithadha
*Assistant Examiner* — Meghan R Kumar
(74) *Attorney, Agent, or Firm* — Novel IP

(57) ABSTRACT

Computer-implemented methods of enabling an on-the-fly generation of at least one user-defined montage from EEG electrodes positioned in a patient's brain, on the patient's brain and/or on the patient's scalp. The methods includes generating a graphical interface to display a view of the patient's brain and/or scalp overlaid with the EEG electrodes, each of which is uniquely identified with reference to its position in the patient's brain, on the patient's brain and/or on the patient's scalp, displaying a tool within the graphical interface for selecting at least one electrode from the displayed EEG electrodes, indicating a reference electrode corresponding to the selected electrode, accessing EEG signals corresponding to the electrode and the reference electrode, and generating another graphical interface to display an EEG trace indicative of a comparison of EEG signals of the electrode and the reference electrode.

21 Claims, 19 Drawing Sheets

(58) Field of Classification Search
CPC ..... A61B 5/7445; A61B 5/7435; A61B 5/369; A61B 5/37; G06F 3/015; H04N 21/42201
See application file for complete search history.

(56) References Cited

U.S. PATENT DOCUMENTS

| | | | |
|---|---|---|---|
| 2,807,259 | A | 9/1957 | Federico |
| 2,950,437 | A | 8/1960 | Stahl |
| 3,165,340 | A | 1/1965 | Kuehl |
| 3,659,250 | A | 4/1972 | Horton |
| 3,682,162 | A | 8/1972 | Colyer |
| 3,985,125 | A | 10/1976 | Rose |
| 3,993,859 | A | 11/1976 | McNeel |
| 4,155,353 | A | 5/1979 | Rea |
| 4,262,306 | A | 4/1981 | Renner |
| 4,263,899 | A | 4/1981 | Burgin |
| 4,545,374 | A | 10/1985 | Jacobson |
| 4,562,832 | A | 1/1986 | Wilder |
| 4,616,635 | A | 10/1986 | Caspar |
| 4,705,049 | A | 11/1987 | John |
| 4,716,901 | A | 1/1988 | Jackson |
| 4,743,959 | A | 5/1988 | Frederiksen |
| 4,765,311 | A | 8/1988 | Kulik |
| 4,817,587 | A | 4/1989 | Janese |
| 4,862,891 | A | 9/1989 | Smith |
| 4,889,502 | A | 12/1989 | Althouse |
| 4,914,508 | A | 4/1990 | Music |
| 5,107,845 | A | 4/1992 | Guern |
| 5,171,279 | A | 12/1992 | Mathews |
| 5,196,015 | A | 3/1993 | Neubardt |
| 5,284,153 | A | 2/1994 | Raymond |
| 5,284,154 | A | 2/1994 | Raymond |
| 5,299,563 | A | 4/1994 | Seton |
| 5,377,667 | A | 1/1995 | Patton |
| 5,438,989 | A | 8/1995 | Hochman |
| 5,462,448 | A | 10/1995 | Kida |
| 5,472,426 | A | 12/1995 | Bonati |
| 5,474,558 | A | 12/1995 | Neubardt |
| 5,540,235 | A | 7/1996 | Wilson |
| 5,544,286 | A | 8/1996 | Laney |
| 5,560,372 | A | 10/1996 | Cory |
| 5,565,779 | A | 10/1996 | Arakawa |
| 5,578,060 | A | 11/1996 | Pohl |
| 5,601,608 | A | 2/1997 | Mouchawar |
| 5,602,585 | A | 2/1997 | Dickinson |
| 5,625,759 | A | 4/1997 | Freeman |
| 5,648,815 | A | 7/1997 | Toba |
| 5,664,029 | A | 9/1997 | Callahan |
| 5,681,265 | A | 10/1997 | Maeda |
| 5,684,887 | A | 11/1997 | Lee |
| 5,728,046 | A | 3/1998 | Mayer |
| 5,741,261 | A | 4/1998 | Moskovitz |
| 5,766,133 | A | 6/1998 | Faisandier |
| 5,772,661 | A | 6/1998 | Michelson |
| 5,775,331 | A | 7/1998 | Raymond |
| 5,775,931 | A | 7/1998 | Jones |
| 5,785,648 | A | 7/1998 | Min |
| 5,792,044 | A | 8/1998 | Foley |
| 5,795,291 | A | 8/1998 | Koros |
| 5,830,150 | A | 11/1998 | Palmer |
| 5,847,755 | A | 12/1998 | Wixson |
| 5,860,973 | A | 1/1999 | Michelson |
| 5,868,668 | A | 2/1999 | Weiss |
| 5,885,210 | A | 3/1999 | Cox |
| 5,891,147 | A | 4/1999 | Moskovitz |
| 5,928,139 | A | 7/1999 | Koros |
| 5,928,158 | A | 7/1999 | Aristides |
| 5,930,379 | A | 7/1999 | Rehg |
| 5,931,777 | A | 8/1999 | Sava |
| 5,933,929 | A | 8/1999 | Kawakami |
| 5,944,658 | A | 8/1999 | Koros |
| 5,954,635 | A | 9/1999 | Foley |
| 5,993,385 | A | 11/1999 | Johnston |
| 6,004,312 | A | 12/1999 | Finneran |
| 6,004,341 | A | 12/1999 | Zhu |
| 6,026,180 | A | 2/2000 | Wittenstein |
| 6,042,540 | A | 3/2000 | Johnston |
| 6,062,216 | A | 5/2000 | Corn |
| 6,074,343 | A | 6/2000 | Nathanson |
| 6,088,878 | A | 7/2000 | Antonucci |
| 6,095,987 | A | 8/2000 | Shmulewitz |
| 6,109,948 | A | 8/2000 | Kuo |
| 6,116,941 | A | 9/2000 | Kuo |
| 6,119,306 | A | 9/2000 | Antonucci |
| 6,139,493 | A | 10/2000 | Koros |
| 6,152,871 | A | 11/2000 | Foley |
| 6,181,961 | B1 | 1/2001 | Prass |
| 6,196,969 | B1 | 3/2001 | Bester |
| 6,200,331 | B1 | 3/2001 | Swartz |
| 6,206,826 | B1 | 3/2001 | Mathews |
| 6,210,202 | B1 | 4/2001 | Kuo |
| 6,224,545 | B1 | 5/2001 | Cocchia |
| 6,236,874 | B1 | 5/2001 | Devlin |
| 6,241,548 | B1 | 6/2001 | Kuo |
| 6,259,945 | B1 | 7/2001 | Epstein |
| 6,264,491 | B1 | 7/2001 | Lord |
| 6,266,558 | B1 | 7/2001 | Gozani |
| 6,273,740 | B1 | 8/2001 | Lord |
| 6,287,322 | B1 | 9/2001 | Zhu |
| 6,302,842 | B1 | 10/2001 | Auerbach |
| 6,306,100 | B1 | 10/2001 | Prass |
| 6,309,349 | B1 | 10/2001 | Bertolero |
| 6,325,764 | B1 | 12/2001 | Griffith |
| 6,334,068 | B1 | 12/2001 | Hacker |
| 6,373,890 | B1 | 4/2002 | Freeman |
| 6,425,859 | B1 | 7/2002 | Foley |
| 6,450,952 | B1 | 9/2002 | Rioux |
| 6,466,817 | B1 | 10/2002 | Kaula |
| 6,473,639 | B1 | 10/2002 | Fischell |
| 6,500,128 | B2 | 12/2002 | Marino |
| 6,535,759 | B1 | 3/2003 | Epstein |
| 6,579,114 | B2 | 6/2003 | Lord |
| 6,609,018 | B2 | 8/2003 | Cory |
| 6,712,795 | B1 | 3/2004 | Cohen |
| 6,799,931 | B2 | 10/2004 | Kwilosz |
| 6,805,668 | B1 | 10/2004 | Cadwell |
| 6,837,716 | B1 | 1/2005 | Brazas |
| 6,847,849 | B2 | 1/2005 | Mamo |
| 6,851,430 | B2 | 2/2005 | Tsou |
| 6,869,301 | B2 | 3/2005 | Shimizu |
| 6,870,109 | B1 | 3/2005 | Villarreal |
| 6,926,728 | B2 | 8/2005 | Zucherman |
| 6,945,933 | B2 | 9/2005 | Branch |
| 7,072,521 | B1 | 7/2006 | Cadwell |
| 7,089,059 | B1 | 8/2006 | Pless |
| 7,104,965 | B1 | 9/2006 | Jiang |
| 7,177,677 | B2 | 2/2007 | Kaula |
| 7,214,197 | B2 | 5/2007 | Prass |
| 7,230,688 | B1 | 6/2007 | Villarreal |
| 7,261,688 | B2 | 8/2007 | Smith |
| 7,374,448 | B2 | 5/2008 | Jepsen |
| 7,470,236 | B1 | 12/2008 | Kelleher |
| 7,522,953 | B2 | 4/2009 | Kaula |
| 7,713,210 | B2 | 5/2010 | Byrd |
| 7,801,601 | B2 | 9/2010 | Maschino |
| 7,914,350 | B1 | 3/2011 | Bozich |
| 7,963,927 | B2 | 6/2011 | Kelleher |
| 7,983,761 | B2 | 7/2011 | Giuntoli |
| 8,108,039 | B2 | 1/2012 | Saliga |
| 8,147,421 | B2 | 4/2012 | Farquhar |
| 8,160,694 | B2 | 4/2012 | Salmon |
| 8,192,437 | B2 | 6/2012 | Simonson |
| D670,656 | S | 11/2012 | Jepsen |
| 8,323,208 | B2 | 12/2012 | Davis |
| 8,439,703 | B2 | 5/2013 | Natoli |
| 8,876,813 | B2 | 11/2014 | Min |
| 8,942,797 | B2 | 1/2015 | Bartol |
| 8,958,869 | B2 | 2/2015 | Kelleher |
| 9,084,551 | B2 | 7/2015 | Brunnett |
| 9,138,586 | B2 | 9/2015 | Eiger |
| 9,155,503 | B2 | 10/2015 | Cadwell |
| 9,295,401 | B2 | 3/2016 | Cadwell |
| 9,352,153 | B2 | 5/2016 | Van Dijk |
| 9,730,634 | B2 | 8/2017 | Cadwell |

(56) References Cited

U.S. PATENT DOCUMENTS

| | | |
|---|---|---|
| 10,238,467 B2 | 3/2019 | Cadwell |
| 2001/0049510 A1 | 12/2001 | Burr |
| 2002/0007188 A1 | 1/2002 | Arambula |
| 2002/0009916 A1 | 1/2002 | Lord |
| 2002/0088098 A1 | 7/2002 | Bouley |
| 2002/0095080 A1 | 7/2002 | Cory |
| 2003/0045808 A1 | 3/2003 | Kaula |
| 2003/0074033 A1 | 4/2003 | Pless |
| 2004/0030258 A1 | 2/2004 | Williams |
| 2004/0127810 A1 | 7/2004 | Sackellares |
| 2004/0192100 A1 | 9/2004 | Shimizu |
| 2005/0003682 A1 | 1/2005 | Brazas |
| 2005/0075578 A1 | 4/2005 | Gharib |
| 2005/0085743 A1 | 4/2005 | Hacker |
| 2005/0148927 A1 | 7/2005 | Ludin |
| 2005/0182454 A1 | 8/2005 | Gharib |
| 2005/0182456 A1 | 8/2005 | Ziobro |
| 2005/0277844 A1 | 12/2005 | Strother |
| 2006/0009754 A1 | 1/2006 | Boese |
| 2006/0085048 A1 | 4/2006 | Cory |
| 2006/0085049 A1 | 4/2006 | Cory |
| 2006/0122514 A1 | 6/2006 | Byrd |
| 2006/0135877 A1 | 6/2006 | Giftakis |
| 2006/0258951 A1 | 11/2006 | Bleich |
| 2006/0276720 A1 | 12/2006 | McGinnis |
| 2007/0016097 A1 | 1/2007 | Farquhar |
| 2007/0021682 A1 | 1/2007 | Gharib |
| 2007/0032841 A1 | 2/2007 | Urmey |
| 2007/0046471 A1 | 3/2007 | Nyalamadugu |
| 2007/0049962 A1 | 3/2007 | Marino |
| 2007/0184422 A1 | 8/2007 | Takahashi |
| 2007/0202005 A1 | 8/2007 | Maschke |
| 2008/0027507 A1 | 1/2008 | Bijelic |
| 2008/0058606 A1 | 3/2008 | Miles |
| 2008/0065144 A1 | 3/2008 | Marino |
| 2008/0071191 A1 | 3/2008 | Kelleher |
| 2008/0082136 A1 | 4/2008 | Gaudiani |
| 2008/0097164 A1 | 4/2008 | Miles |
| 2008/0108244 A1 | 5/2008 | Jepsen |
| 2008/0167574 A1 | 7/2008 | Farquhar |
| 2008/0183096 A1 | 7/2008 | Snyder |
| 2008/0194970 A1 | 8/2008 | Steers |
| 2008/0269777 A1 | 10/2008 | Appenrodt |
| 2008/0281313 A1 | 11/2008 | Fagin |
| 2008/0312520 A1 | 12/2008 | Rowlandson |
| 2009/0018399 A1 | 1/2009 | Martinelli |
| 2009/0043221 A1 | 2/2009 | Kaplan |
| 2009/0088660 A1 | 4/2009 | McMorrow |
| 2009/0105604 A1 | 4/2009 | Bertagnoli |
| 2009/0177112 A1 | 7/2009 | Gharib |
| 2009/0196471 A1 | 8/2009 | Goetz |
| 2009/0204016 A1 | 8/2009 | Gharib |
| 2009/0209879 A1 | 8/2009 | Kaula |
| 2009/0259108 A1 | 10/2009 | Miles |
| 2009/0279767 A1 | 11/2009 | Kukuk |
| 2010/0036384 A1 | 2/2010 | Gorek |
| 2010/0106011 A1 | 4/2010 | Byrd |
| 2010/0113898 A1 | 5/2010 | Kim |
| 2010/0152604 A1 | 6/2010 | Kaula |
| 2010/0168603 A1 | 7/2010 | Himes |
| 2010/0191305 A1 | 7/2010 | Imran |
| 2010/0249638 A1 | 9/2010 | Liley |
| 2010/0286554 A1 | 11/2010 | Davis |
| 2010/0317931 A1 | 12/2010 | Sarkela |
| 2010/0317989 A1 | 12/2010 | Gharib |
| 2011/0082383 A1 | 4/2011 | Cory |
| 2011/0184308 A1 | 7/2011 | Kaula |
| 2011/0295579 A1 | 12/2011 | Tang |
| 2011/0313530 A1 | 12/2011 | Gharib |
| 2012/0003862 A1 | 1/2012 | Newman |
| 2012/0046531 A1 | 2/2012 | Hua |
| 2012/0071779 A1 | 3/2012 | Sarkela |
| 2012/0109000 A1 | 5/2012 | Kaula |
| 2012/0109004 A1 | 5/2012 | Cadwell |
| 2012/0209082 A1 | 8/2012 | Al-Ali |
| 2012/0209346 A1 | 8/2012 | Bikson |
| 2012/0220891 A1 | 8/2012 | Kaula |
| 2012/0238855 A1 | 9/2012 | Lanning |
| 2012/0238893 A1 | 9/2012 | Farquhar |
| 2012/0265040 A1 | 10/2012 | Ito |
| 2012/0296230 A1 | 11/2012 | Davis |
| 2013/0012880 A1 | 1/2013 | Blomquist |
| 2013/0109996 A1 | 5/2013 | Turnbull |
| 2013/0138010 A1 | 5/2013 | Nierenberg |
| 2013/0152657 A1 | 6/2013 | Swinehart |
| 2013/0204315 A1 | 8/2013 | Wongsarnpigoon |
| 2013/0253447 A1 | 9/2013 | Ball |
| 2013/0304407 A1 | 11/2013 | George |
| 2014/0121555 A1 | 5/2014 | Scott |
| 2014/0275926 A1 | 9/2014 | Scott |
| 2014/0276181 A1 | 9/2014 | Sun |
| 2015/0150512 A1 | 6/2015 | Warner |
| 2015/0230749 A1 | 8/2015 | Gharib |
| 2015/0238106 A1 | 8/2015 | Lappalainen |
| 2015/0351643 A1 | 12/2015 | Edwards |
| 2015/0372433 A1 | 12/2015 | Lisogurski |
| 2016/0000382 A1 | 1/2016 | Jain |
| 2016/0174861 A1 | 6/2016 | Cadwell |
| 2016/0270679 A1 | 9/2016 | Mahon |
| 2016/0328991 A1 | 11/2016 | Simpson |
| 2017/0056663 A1 | 3/2017 | Kaemmerer |
| 2017/0100047 A1 | 4/2017 | Edwards |
| 2018/0117309 A1 | 5/2018 | Rapoport |
| 2018/0140829 A1 | 5/2018 | Ramos De Miguel, Sr. |
| 2018/0161123 A1 | 6/2018 | Cadwell |
| 2018/0198218 A1 | 7/2018 | Regan |
| 2018/0256097 A1 | 9/2018 | Bray |
| 2018/0296277 A1 | 10/2018 | Schwartz |
| 2019/0190187 A1 | 6/2019 | Fukazawa |
| 2020/0022603 A1 | 1/2020 | Cardenas |
| 2020/0108246 A1 | 4/2020 | Cadwell |
| 2020/0297282 A1 | 9/2020 | Batzer |
| 2020/0330772 A1 | 10/2020 | Hartmann-Bax |

FOREIGN PATENT DOCUMENTS

| | | |
|---|---|---|
| EP | 298268 | 1/1989 |
| EP | 0863719 A1 | 9/1998 |
| EP | 890341 | 1/1999 |
| EP | 972538 | 1/2000 |
| EP | 1182965 B1 | 3/2002 |
| EP | 2173238 A2 | 4/2010 |
| JP | H11513592 A | 11/1999 |
| JP | 2008546509 A | 12/2008 |
| WO | 2000038574 A1 | 7/2000 |
| WO | 2000066217 A1 | 11/2000 |
| WO | 2001037728 A1 | 5/2001 |
| WO | 2003005887 A2 | 1/2003 |
| WO | 2005030318 A1 | 4/2005 |
| WO | 2006042241 A2 | 4/2006 |
| WO | 2016028822 A1 | 2/2016 |
| WO | 2016105571 A1 | 6/2016 |

OTHER PUBLICATIONS

Compumedics Website, "Compumedics Profusion EEG 4" accessed online Oct. 9, 2021, available online Feb. 23, 2017 https://www.compumedics.com.au/wp-content/uploads/2016/08/AD125-02-Profusion-EEG4-brochureLR.pdf (Year: 2017).*

Intelimed Website, "Compumedics Profusion EEG 5 Top Features" accessed online Oct. 9, 2021, available online Sep. 30, 2014 http://www.intelimed.com.mx/AG479%20-02%20Whats%20new%20in%20Profusion%20EEG5.pdf (Year: 2014).*

Brainstorm website, https://web.archive.org/web/20180421074035/https://neuroimage.usc.edu/brainstorm/Tutorials/MontageEditor, available online Apr. 21, 2018 (Year: 2018).*

Brainstorm website, https://web.archive.org/web/20180330235454/http://neuroimage.usc.edu/brainstorm/Tutorials/CreateProtocol, available on Mar. 30, 2018 (Year: 2018).*

Brainstorm website, https://web.archive.org/web/20180416072211/http://neuroimage.usc.edu/brainstorm/Screenshots, available on Apr. 16, 2018 (Year: 2018).*

(56) References Cited

OTHER PUBLICATIONS

Brainstorm website, https://web.archive.org/web/20180411211909/https://neuroimage.usc.edu/brainstorm/Introduction, available on Apr. 11, 2018 (Year: 2018).*

Brainstorm website, https://web.archive.org/web/20180505021718/https://neuroimage.usc.edu/brainstorm/Tutorials/Epileptogenicity, available on May 5, 2018 (Year: 2018).*

Aage R. Møller, "Intraoperative Neurophysiologic Monitoring", University of Pittsburgh, School of Medicine Pennsylvania, © 1995 by Harwood Academic Publishers GmbH.

Clements, et. al., "Evoked and Spontaneous Electromyography to Evaluate Lumbosacral Pedicle Screw Placement", 21 (5):600-604 (1996).

Danesh-Clough, et. al., "The Use of Evoked EMG in Detecting Misplaced Thoracolumbar Pedicle Screws", 26(12):1313-1316 (2001).

Dezawa et al., "Retroperitoneal Laparoscopic Lateral Approach to the Lumbar Spine: A New Approach, Technique, and Clinical Trial", Journal of Spinal Disorders 13(2):138-143 (2000).

Dickman, et al., "Techniques in Neurosurgery", National Library of Medicine, 3 (4) 301-307 (1997).

Epstein, et al., "Evaluation of Intraoperative Somatosensory-Evoked Potential Monitoring During 100 Cervical Operations", 18(6):737-747 (1993), J.B. Lippincott Company.

Glassman, et. al., "A Prospective Analysis of Intraoperative Electromyographic Monitoring of Pedicle Screw Placement with Computed Tomographic Scan Confirmation", 20(12):1375-1379.

Goldstein, et. al., "Minimally Invasive Endoscopic Surgery of the Lumbar Spine", Operative Techniques in Orthopaedics, 7 (1):27-35 (1997).

Greenblatt, et. al., "Needle Nerve Stimulator-Locator", 41 (5):599-602 (1962).

H.M. Mayer, "Minimally Invasive Spine Surgery, A Surgical Manual", Chapter 12, pp. 117-131 (2000).

Hinrichs, et al., "A trend-detection algorithm for intraoperative EEG monitoring", Med. Eng. Phys. 18 (8):626-631 (1996).

Bergey et al., "Endoscopic Lateral Transpsoas Approach to the Lumbar Spine", Spine 29 (15):1681-1688 (2004).

Holland, "Spine Update, Intraoperative Electromyography During Thoracolumbar Spinal Surgery", 23 (17):1915-1922 (1998).

Holland, et al., "Continuous Electromyographic Monitoring to Detect Nerve Root Injury During Thoracolumbar Scoliosis Surgery", 22 (21):2547-2550 (1997), Lippincott-Raven Publishers.

Hovey, A Guide to Motor Nerve Monitoring, pp. 1-31, Mar. 20, 1998, The Magstim Company Limited.

Kevin T. Foley, et. al., "Microendoscipic Discectomy" Techniques in Neurosurgery, 3:(4):301-307, © 1997 Lippincott-Raven Publishers, Philadelphia.

Kossmann et al., "The use of a retractor system (SynFrame) for open, minimal invasive reconstruction of the anterior column of the thoracic and lumbar spine", 10:396-402 (2001).

Kossmann, et. al., "Minimally Invasive Vertebral Replacement with Cages in Thoracic and Lumbar Spine", European Journal of Trauma, 2001, No. 6, pp. 292-300.

Lenke, et. al., "Triggered Electromyographic Threshold for Accuracy of Pedicle Screw Placement, An Animal Model and Clinical Correlation", 20 (14):1585-1591 (1995).

Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.

MaGuire, et. al., "Evaluation of Intrapedicular Screw Position Using Intraoperative Evoked Electromyography", 20 (9):1068-1074 (1995).

Mathews et al., "Laparoscopic Discectomy With Anterior Lumbar Interbody Fusion, A Preliminary Review", 20 (16):1797-1802, (1995), Lippincott-Raven Publishers.

Bertagnoli, et. al., "The AnteroLateral transPsoatic Approach (ALPA), A New Technique for Implanting Prosthetic Disc-Nucleus Devices", 16 (4):398-404 (2003).

Michael R. Isley, et. al., "Recent Advances in Intraoperative Neuromonitoring of Spinal Cord Function: Pedicle Screw Stimulation Techniques", Am. J. End Technol. 37:93-126 (1997).

Minahan, et. al., "The Effect of Neuromuscular Blockade on Pedicle Screw Stimulation Thresholds" 25(19):2526-2530 (2000).

Pimenta et. al., "Implante de protese de nucleo pulposo: analise inicial", J Bras Neurocirurg 12 (2):93-96, (2001).

Raymond J. Gardocki, MD, "Tubular diskectomy minimizes collateral damage", AAOS Now, Sep. 2009 Issue, http://www.aaos.org/news/aaosnow/sep09/clinical12.asp.

Raymond, et. al., "The NerveSeeker: A System for Automated Nerve Localization", Regional Anesthesia 17:151-162 (1992).

Reidy, et. al., "Evaluation of electromyographic monitoring during insertion of thoracic pedicle screws", British Editorial Society of Bone and Joint Surgery 83 (7):1009-1014, (2001).

Rose et al., "Persistently Electrified Pedicle Stimulation Instruments in Spinal Instrumentation: Technique and Protocol Development", Spine: 22(3): 334-343 (1997).

Teresa Riordan "Patents; A businessman invents a device to give laparoscopic surgeons a better view of their worK", New York Times www.nytimes.com/2004/29/business/patents-businessman-invents-device-give-la (Mar. 2004).

Toleikis, et. al., "The usefulness of Electrical Stimulation for Assessing Pedicle Screw Placements", Journal of Spinal Disorders, 13 (4):283-289 (2000).

U.Schick, et al., "Microendoscopic lumbar discectomy versus open surgery: an intraoperative EMG study", pp. 20-26, Published online: Jul. 31, 2001 © Springer-Verlag 2001.

Bose, et. al., "Neurophysiologic Monitoring of Spinal Nerve Root Function During Instrumented Posterior Lumbar Spine Surgery", 27 (13):1440-1450 (2002).

Vaccaro, et. al., "Principles and Practice of Spine Surgery", Mosby, Inc. ©2003, Chapter 21, pp. 275-281.

Vincent C. Traynelis, "Spinal arthroplasty", Neurosurg Focus 13 (2):1-7. Article 10, (2002).

Welch, et. al., "Evaluation with evoked and spontaneous electromyography during lumbar instrumentation: a prospective study", J Neurosurg 87:397-402, (1997).

Zouridakis, et. al., "A Concise Guide to Intraoperative Monitoring", Library of Congress card No. 00-046750, Chapters, p. 21, chapter 4, p. 58 and chapter 7 pp. 119-120.

Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.

Chapter 9, "Root Finding and Nonlinear Sets of Equations", Chapter 9:350-354, http://www.nr.com.

Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".

Ford et al, Electrical characteristics of peripheral nerve stimulators, implications for nerve localization, Dept. of Anesthesia, University of Cincinnati College of Medicine, Cincinnati, OH 45267, pp. 73-77.

Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.

Urmey "Using the nerve stimulator for peripheral or plexus nerve blocks" Minerva Anesthesiology 2006; 72:467-71.

Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.

Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).

(56) References Cited

OTHER PUBLICATIONS

Calancie, et. al., "Threshold-level repetitive transcranial electrical stimulation for intraoperative monitoring of central motor conduction", J. Neurosurg 95:161-168 (2001).
Calancie, et. al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, dated Feb. 19, 2020.
International Search Report for PCT/US2017/062559, dated Jan. 26, 2018.
Deff Corporation, No more confusion about which direction to plug in. A USB cable that can be plugged in both ways is now available. A connector is equipped with an LED indicator to check a charging status of a smartphone. Nov. 6, 2015 (Dec. 28, 2021 Search) Internet URL:https://deff.co.jp/news/dca-mbled (Document showing known technology).
"Long, S; "Phase Locked Loop Circuits", Apr. 27, 2005". (Year: 2005).

\* cited by examiner

Auto Generated Montages

All Referential: 665a [>]
All Bipolar: 665b [>]
Subdural Referential: 665c [>]
Subdural Bipolar: 665d [>]
Depth Referential: 665e [>]
Depth Bipolar: 665f [>]
Mixed: 665g [>]
Sparse Referential: 665h [>]
Add Spaces Between Electrodes: 665i [>]

METHODS FOR AUTOMATIC GENERATION OF EEG MONTAGES

CROSS REFERENCE

The present application relies on U.S. Patent Provisional Application No. 62/771,897, entitled "Methods for Automatic Generation of EEG Montages" and filed on Nov. 27, 2018, for priority, which is herein incorporated by reference in its entirety.

FIELD

The present specification is related generally to the field of electroencephalography. More specifically the present specification is related to systems and methods for automatically generating one or more montages subsequent to a user's inputs, on at least one GUI, indicative of the user's selection of one or more EEG channels or electrodes.

BACKGROUND

An electroencephalograph (EEG) is a device which measures and records brain wave activity by sensing electrical potential of a patient's scalp, cortex or cerebrum at various sites. Each EEG channel corresponds to a particular electrode combination attached to the patient. The EEG may be recorded with reference to a common passive electrode, which is referred to as a monopolar (referential) recording, or the EEG may be recorded differentially between pairs of contiguous electrodes, which are referred to as bipolar recordings. In the case of bipolar recordings, there are various ways to select the electrode pairs according to montages designed to visualize the propagation of neural activity in different directions of the patient's brain.

Montages are visual, graphical representations of waveforms, also referred to as channels or derivations, which are generated as a function of the potential difference between two or more electrodes. When aggregated together from electrodes spanning a patient's scalp, these montages graphically represent the patient's EEG activity, allow a comparison of EEG activity on the two sides of the brain (lateralization), and can aid in a localization of recorded activity to a specific brain region. Different montages may be useful for visualizing the sources of different EEG patterns. However, with 21 electrode positions in the 10-20 system and 16 total channels, the number of possible montages is $21^{16}$. The 10-10 system, with more than 70 electrode positions, and the ability to display up to 256 channels in modern digital EEG machines, provides the ability to create an even greater number of montages, such as $70^{256}$. The "10" and "20" refer to the actual distances between adjacent electrodes, which are either 10% or 20% of the total front-back or right-left distance of the skull.

While 10-10 and 10-20 EEG monitoring systems using electrodes placed on the patient's scalp are useful in many neuromonitoring situations, there are indications (for example, neuromonitoring and mapping of epileptic brains to determine surgery candidates) where more precise neuromonitoring is required. Electrocorticography (ECoG) and stereoelectroencephalography (sEEG) are methods of intracranial EEG monitoring and cortical mapping that require high channel count recording and stimulating devices. These systems use amplifiers capable of receiving input electrodes typically in a range of 21 to 256 electrodes and sometimes more than 500 electrodes. In ECoG, electrodes are placed on the cerebral cortex via a craniotomy. In sEEG, depth electrodes may be placed via small holes (burr holes) drilled in the skull. ECoG and sEEG may be used when standard EEG monitoring results are inconclusive, particularly for epilepsy patients. Since ECoG and sEEG use strip or grid electrodes and depth electrodes on the surface of the brain and in the brain respectively, they provide a benefit of using electrodes that are closer to the area(s) producing seizures than electrodes placed on the scalp in standard EEG monitoring. In addition, electrodes placed directly on or in the brain have the advantage of recording signals without the interference of skin, fat tissue, muscle or bone. ECoG and sEEG may be used to monitor, assess and map the brains of epilepsy patients who have may benefit from surgery and have not responded to less invasive treatments including pharmaceuticals. Mapping will indicate to physicians areas of an epileptic brain for resection and functional areas of the brain to be safeguarded during surgery. Functional mapping involves using the electrodes (grid or strip) to stimulate the brain and record signals to identify the underlying function of a brain region, such as language, sensation, or motor function, to precisely map an origin of seizures. ECoG and sEEG typically involve long term monitoring where electrodes are placed intracranially during a surgery, then the monitoring device remains connected to the patient for monitoring and recording to identify areas of pathological brain activity. Later, the electrodes are removed and the device may be used during surgery to monitor or stimulate nerves to direct the surgery. When a discrete epileptogenic region of the brain is identified and can be removed without the introduction of unacceptable additional neurological deficits, respective surgery is performed.

In high channel count systems it is a challenge to create montages and display acquired EEG data in ways that are visually useful and discernible. While the user can see general activity on specific traces, it may be visually arduous for a user to discern details of EEG activity when there are upwards of 128 traces on a screen. With high channel count systems (that include surgically implanted electrodes as well as scalp locations, for example) conventional predefined montages are not practical as there is not a standard set of electrode sites defined from which to create a montage subset. Electrodes are surgically implanted differently for each patient. Accordingly, the montages need to be customized based on a review of live data and a desire to look in more detail at a subset of the total set of electrode signals. Thus, it is desirable to create multiple custom montages during a neurological study using high channel count systems. However, legacy high channel count systems are too inflexible to allow for the kind of customized exploration often required. Additionally, in conventional high channel count systems, it can take an extended amount of time to manually select EEG signal inputs in order to build a montage.

Thus, there is a need for systems and methods to generate one or more interfaces, preferably a graphical user interface (GUI) integrated into a display device, that enable a user to select any combination of two or more EEG signal inputs from which a channel or derivation may be dynamically generated and, accordingly, from which a montage may be dynamically generated. There is also a need for one or more interfaces that facilitate isolation of EEG traces by a user, that provide desired flexibility and that allow for customized exploration enabling a user to see detailed morphology of the EEG data where there is activity. There is also a need for systems and methods for automatically generating or creating multiple custom montages, during and/or after recordation of EEG signals, as a result of the user's inputs or selections on the one or more GUIs.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a computer readable non-transitory medium comprising a plurality of executable programmatic instructions wherein, when the plurality of executable programmatic instructions are executed by a processor in a computing device, at least one user-defined montage from a plurality of EEG electrodes positioned in a patient's brain, on the patient's brain or on the patient's scalp is generated, the plurality of executable programmatic instructions comprising: programmatic instructions, stored in the computer readable non-transitory medium, for generating a first graphical interface to display at least one graphical view of the patient's brain and/or scalp overlaid with a plurality of identifications corresponding to the plurality of EEG electrodes, wherein each of the plurality of identifications uniquely references a position of each of the plurality of EEG electrodes relative to the patient's brain and/or scalp; programmatic instructions, stored in the computer readable non-transitory medium, for displaying a tool within the first graphical interface, wherein the tool is configured to be manipulated in order to select at least one identification of the plurality of identifications; programmatic instructions, stored in the computer readable non-transitory medium, for prompting the user to indicate at least one reference identification corresponding to the at least one identification; programmatic instructions, stored in the computer readable non-transitory medium, for acquiring EEG signals associated with EEG electrodes corresponding to the at least one identification and the at least one reference identification; and programmatic instructions, stored in the computer readable non-transitory medium, for generating a second graphical interface to display at least one EEG trace indicative of a comparison of EEG signals associated with EEG electrodes corresponding to the at least one identification and the at least one reference identification.

Optionally, the computer readable non-transitory medium further comprises programmatic instructions configured to enable a user to input a selection of the at least one identification comprising at least one of programmatic instructions for enabling a drawing a loop around the at least one identification, programmatic instructions for enabling a clicking from the at least one identification to multiple other identifications of the plurality of identifications to thereby visually connect the at least one identifications and multiple other identifications, programmatic instructions for enabling a clicking and/or dragging an icon over or looping around at least one of the plurality of EEG electrodes, programmatic instructions for enabling a clicking a body of at least one of the plurality of EEG electrodes or programmatic instructions for enabling a pressing a key on a keyboard and clicking upon more than one of the plurality of EEG electrodes.

The user may select first and second identifications, said first and second identification being adjacent to each other.

Optionally, the computer readable non-transitory medium further comprises programmatic instructions configured to prompt the user to indicate one of said first and second identifications as the at least one reference identification.

The plurality of EEG electrodes may comprise at least one of strip, grid or depth electrodes.

Optionally, the computer readable non-transitory medium further comprises programmatic instructions for acquiring the EEG signals in real time while said EEG signals are being recorded using the plurality of EEG electrodes.

Optionally, the computer readable non-transitory medium further comprises programmatic instructions configured to acquire the EEG signals from a database system, wherein the database system is configured to store the EEG signals for offline processing.

The at least one identification may be a single identification.

Optionally, the computer readable non-transitory medium further comprises programmatic instructions configured to prompt the user to indicate reference identification from said plurality of identifications, wherein said reference identification is same for all subsequently selected single identifications.

The present specification also discloses a computer-implemented method of enabling a generation of at least one user-defined montage from a plurality of EEG electrodes positioned in a patient's brain, on the patient's brain and/or on the patient's scalp, said method comprising: generating a first graphical interface to visually display at least one view of the patient's brain and/or scalp overlaid with a spatial distribution of the plurality of EEG electrodes, wherein each of said plurality of EEG electrodes in the at least one view is uniquely identified with reference to its position in the patient's brain, on the patient's brain and/or on the patient's scalp; displaying a tool within the first graphical interface; receiving an input from a user using the tool to select at least one electrode from the plurality of EEG electrodes displayed in the at least one view; prompting the user to indicate at least one reference electrode corresponding to the selected at least one electrode; accessing EEG signals corresponding to the at least one electrode and the at least one reference electrode; and generating a second graphical interface to display at least one EEG trace indicative of a comparison of EEG signals of the at least one electrode and the at least one reference electrode.

Selecting the at least one electrode from the plurality of EEG electrodes may be achieved by at least one of drawing a loop around the at least one electrode, clicking on multiple electrodes of the plurality of EEG electrodes to visually connect them, clicking and dragging an icon over or looping the at least one electrode, clicking a body of the at least one electrode, or by pressing a key on a keyboard and clicking upon at least one electrode and additional electrodes of the plurality of EEG electrodes.

Optionally, the computer-implemented method further comprises receiving a selection of the at least one electrode and a second electrode from the plurality of EEG electrodes in the at least one view, wherein the at least one electrode and the second electrode are adjacent to each other. Optionally, the computer-implemented method further comprises prompting the user to indicate one of the at least one electrode and the second electrodes as the at least one reference electrode.

The plurality of EEG electrodes may comprise at least one of strip, grid or depth electrodes.

Optionally, the computer-implemented method further comprises acquiring the EEG signals in real time while the EEG signals are being recorded using said plurality of EEG electrodes.

Optionally, the computer-implemented method further comprises acquiring the EEG signals from a database system configured to store the EEG signals for offline processing.

Optionally, the computer-implemented method further comprises receiving a selection of only the at least one electrode in the at least one view. Optionally, the computer-implemented method further comprises prompting the user to indicate the at least one reference electrode from the plurality of electrodes, wherein the at least one reference electrode is designated to be a same reference electrode for all subsequently selected electrodes from the plurality of electrodes.

The present specification also discloses a computer-implemented method of enabling a real-time generation of at least one user-defined bipolar montage from a plurality of EEG electrodes positioned in a patient's brain, on the patient's brain and/or on the patient's scalp, said method comprising: generating a first graphical interface to display at least one view of said patient's brain and/or scalp overlaid with a plurality of identifications corresponding to the plurality of EEG electrodes, wherein each of said identifications uniquely references each of the plurality of EEG electrodes in the patient's brain, on the patient's brain and/or on the patient's scalp; displaying a tool within the first graphical interface, wherein the tool is configured to receive a user's input that selects a first identification and a second identification; prompting the user to indicate a reference identification from the selected first identification and the second identification; acquiring EEG signals associated with the plurality of EEG electrodes corresponding to the first identification, the second identification and the reference identification; and generating a second graphical interface to display an EEG trace associated with the first identification, the second identifications and the reference identification, wherein the plurality of EEG electrodes include at least one of strip, grid or depth electrodes.

Selecting the first identification and the second identification may be achieved by at least one of drawing a loop around the first identification and the second identification, clicking on the first identification and the second identification to visually connect them, clicking and dragging an icon over or looping the first identification and the second identification, clicking a body of the first identification and the second identification, or by pressing a key on a keyboard and clicking upon the first identification and the second identification.

Optionally, the computer-implemented method further comprises acquiring the EEG signals in real time while the EEG signals are being recorded using the plurality of EEG electrodes.

Optionally, the computer-implemented method further comprises acquiring the EEG signals from a database system configured to store the EEG signals for offline processing.

The present specification also discloses a computer readable non-transitory medium comprising a plurality of executable programmatic instructions wherein, when said plurality of executable programmatic instructions are executed by a processor in a computing device, a process is performed for generating at least one user-defined montage from a plurality of EEG electrodes positioned on a patient's scalp, said plurality of executable programmatic instructions comprising: programmatic instructions, stored in said computer readable non-transitory medium, for generating a first graphical interface to display at least one view of said patient's scalp overlaid with a plurality of identifications corresponding to said plurality of EEG electrodes, wherein each of said identifications is unique with reference to positions of said plurality of EEG electrodes on said patient's scalp; programmatic instructions, stored in said computer readable non-transitory medium, for displaying a drawing tool within said first graphical interface, wherein a user utilizes said drawing tool to select at least one identification; programmatic instructions, stored in said computer readable non-transitory medium, for prompting the user to indicate at least one reference identification corresponding to said at least one identification; programmatic instructions, stored in said computer readable non-transitory medium, for acquiring EEG signals associated with EEG electrodes corresponding to said at least one identification and said at least one reference identification; and programmatic instructions, stored in said computer readable non-transitory medium, for generating a second graphical interface to display at least one EEG trace indicative of a comparison of EEG signals associated with EEG electrodes corresponding to said at least one identification and said at least one reference identification.

Optionally, the user draws a loop around said at least one identification to indicate selection of said at least one identification. In various embodiments, the loop may have any one of a plurality shapes such as, but not limited to, circular/oval, rectangular with sharp corners, rectangular with rounded corners, square, spherical, cylindrical, and free form. In various embodiments, the user may click from identification to identification in a 'connect the dots' or 'dot to dot' manner to select identifications. In various embodiments, an entire strip, grid, or depth electrode may be selected by clicking and dragging a cursor over or 'looping' the electrode. In some embodiments, the user may click on a strip, grid or depth electrode body (instead of on a specific identifier electrode site) to select an entirety of the strip, grid or depth electrode. In some embodiments, the user may press the 'shift' key (on his keyboard) and click to select multiple electrode collections.

Optionally, the user selects first and second identifications, said first and second identification being adjacent to each other.

Optionally, the user is prompted to indicate one of said first and second identifications as a reference identification.

Optionally, said plurality of EEG electrodes are positioned on said patient's scalp in accordance with the International 10-20 system.

Optionally, said EEG signals are acquired in real time while said EEG signals are being recorded using said plurality of EEG electrodes.

Optionally, said EEG signals are acquired from a database system that stores said EEG signals for offline processing.

Optionally, the user selects a single identification. Optionally, the user is prompted to indicate reference identification from said plurality of identifications, and wherein said reference identification is same for all subsequently selected single identifications.

The present specification also discloses a computer-implemented method of enabling generation of at least one user-defined montage from a plurality of EEG electrodes positioned on a patient's scalp, said method comprising: generating a first graphical interface to display at least one view of said patient's scalp overlaid with a spatial distribution of said plurality of EEG electrodes, wherein each of said plurality of EEG electrodes on said at least one view is uniquely identified with reference to its position on said patient's scalp; displaying a drawing tool within said first graphical interface; enabling a user to use said drawing tool to select at least one electrode from said plurality of EEG electrodes displayed in said at least one view; prompting the user to indicate at least one reference electrode corresponding to said at least one electrode; accessing EEG signals corresponding to said at least one electrode and said at least one reference electrode; and generating a second graphical interface to display at least one EEG trace indicative of a comparison of EEG signals of said at least one electrode and said at least one reference electrode.

Optionally, the user draws a loop around said at least one EEG electrode to indicate selection of said at least one EEG electrode.

Optionally, the user selects first and second electrodes from said plurality of EEG electrodes in said at least one view, said first and second electrodes being adjacent to each other.

Optionally, the user is prompted to indicate one of said first and second electrodes as reference electrode.

Optionally, said plurality of EEG electrodes is positioned on said patient's scalp in accordance with the International 10-20 system.

Optionally, said EEG signals are acquired in real time while said EEG signals are being recorded using said plurality of EEG electrodes.

Optionally, said EEG signals are acquired from a database system that stores said EEG signals for offline processing.

Optionally, the user selects a single electrode from said plurality of EEG electrodes in said at least one view.

Optionally, the user is prompted to indicate reference electrode from said plurality of electrodes in said at least one view, and wherein said reference electrode is same for all subsequently selected single electrodes.

The present specification also discloses a computer-implemented method of enabling on-the-fly generation of at least one user-defined bipolar montage from a plurality of EEG electrodes positioned on a patient's scalp, said method comprising: generating a first graphical interface to display at least one view of said patient's scalp overlaid with a plurality of identifications corresponding to said plurality of EEG electrodes, wherein each of said identifications is unique with reference to positions of said plurality of EEG electrodes on said patient's scalp; displaying a drawing tool within said first graphical interface, wherein a user utilizes said drawing tool to select first and second identifications; prompting the user to indicate reference identification from the selected first and second identifications; acquiring EEG signals associated with EEG electrodes corresponding to said first and second identifications and said reference identification; and generating a second graphical interface to display an EEG trace associated with said first and second identifications and said reference identification.

Optionally, the user draws a loop around said first and second identification to indicate selection.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 6F shows a GUI to enable a user to select one or more of a plurality of auto-generated montage settings, in accordance with some embodiments of the present specification;

DETAILED DESCRIPTION

Figure 1:
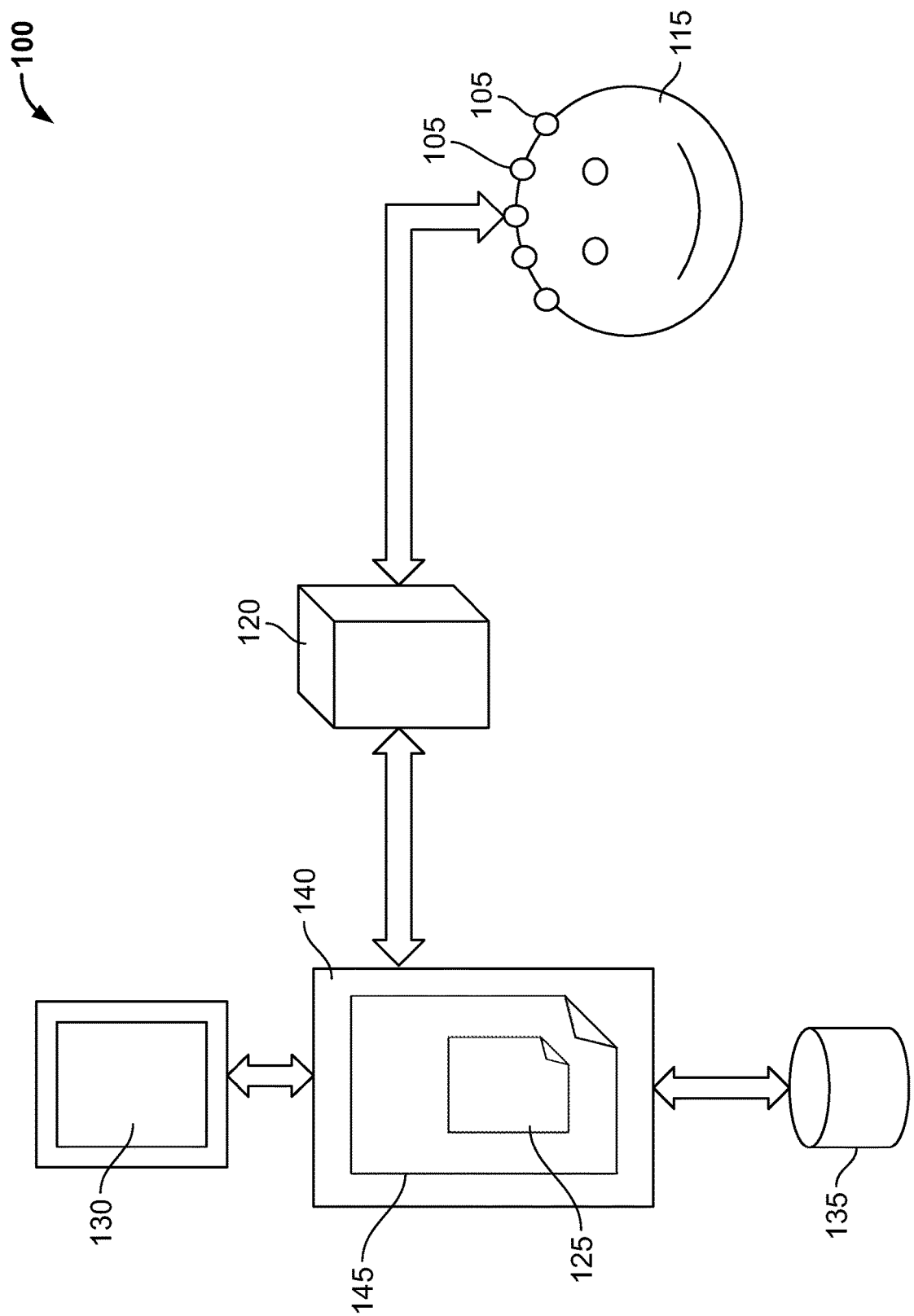
FIG. 1 illustrates an EEG system for detecting, diagnosing, and/or predicting neurological events from EEG signals, in accordance with some embodiments of the present specification.

The term 'user' is used interchangeably to refer to a surgeon, neuro-physician, neuro-surgeon, neuro-physiologist, technician or operator of the EEG system and/or other patient-care personnel or staff.

A "computing device" refers to at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a GUI. The GUI also presents various menus that allow users to configure settings according to their requirements. The system further comprises at least one processor to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

"Electrode" refers to a conductor used to establish electrical contact with a nonmetallic part of a circuit. EEG electrodes are small metal discs usually made of stainless steel, tin, gold or silver covered with a silver chloride coating. They are typically placed on the scalp on predetermined locations.

A "subdural electrode grid" refers to a thin sheet of material with multiple small (roughly a couple mm in size) recording electrodes implanted within it. These are placed directly on the surface of the brain and have the advantage of recording the EEG without the interference of the skin, fat tissue, muscle, and bone that may limit scalp EEG. Shapes and sizes of these sheets are chosen to best conform to the surface of the brain and the area of interest.

A "depth electrode" refers to small wires that are implanted within the brain itself. Each wire has electrodes which surround it. These electrodes are able to record brain activity along the entire length of the implanted wire. They have the advantage of recording activity from structures deeper in the brain. They can be implanted through small skin pokes.

"Montage" refers to one or more data sets, each typically represented in the form of a waveform, that are generated by a processor applying a function, such as a comparison function, to data inputs received from two or more electrodes. For example, a bipolar montage is a collection of waveforms, or channels, generated as a function of data from two electrodes, typically adjacent each other. A referential montage uses a common reference electrode, in combination with other electrodes, to generate the channels.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

Electroencephalography System

FIG. 1 illustrates an electroencephalography (EEG) system 100 for detecting, diagnosing, or predicting neurological events from EEG signals, in accordance with some embodiments of the present specification. The figure shows a plurality of EEG sensors or electrodes 105 spatially positioned in and/or on a layer of tissue such as in the brain, on the brain and/or on the scalp of a patient 115. The plurality of electrodes 105 are in data communication with a multi-channel amplifier 120 that is in data communication with a computing device 140. The computing device 140 is in data communication with a display unit 130 and at least one database 135.

In various embodiments, the plurality of electrodes 105 are small metal discs typically made of stainless steel, tin, gold or silver covered with a silver chloride coating. In various embodiments, the plurality of electrodes 105 comprises subdural (strip and grid electrodes) and depth electrodes placed directly on or in the patient's brain. The plurality of electrodes 105 record electrical signals (EEG signals) from the patient's brain and communicate the analog signals over a first communication link to the multi-channel amplifier 120 that amplifies the signals, converts the signals from an analog EEG data set to a digital EEG data set, and communicates the resultant digital EEG signal to the computing device 140 over a second communication link. In embodiments, the first and second communication links may be wired or wireless links.

The computing device 140 includes an input/output controller, at least one communications interface and system memory. The system memory includes at least one random access memory (RAM) and at least one read-only memory (ROM). These elements are in communication with a central processing unit (CPU) to enable operation of the computing device 140. In various embodiments, the computing device 140 may be a conventional standalone computer or alternatively, the functions of the computing device 140 may be distributed across multiple computer systems and architectures. For example, in a distributed architecture, the at least one database 135 and processing circuitry are housed in separate units or locations. Some units perform primary processing functions and contain at a minimum a general controller or a processing circuitry and a system memory.

The computing device 140 executes EEG software 145 to process, store, retrieve and display, on the display unit 130, the patient's EEG data. In embodiments, the EEG software 145 processes the received signals, extracts parameters that characterize the EEG data, and generates a display of the data for a user. The processed EEG data is either displayed on the display unit 130 in real-time or stored in the at least one database 135 for later analyses. It should be appreciated that the term real-time means a process is occurring substantially concurrent to another process, such as concurrent to a measurement or EEG signal acquisition process.

In accordance with an aspect of the present specification, the EEG software 145 comprises an automated montage creation module 125 that implements a plurality of programmatic instructions or code to generate one or more GUIs (Graphical User Interfaces), including views of the spatial distribution or positioning of the electrodes 105 in the brain, on the brain and/or on the patient's scalp, and enable the user to provide inputs indicative of selection of one or more electrode combinations or montages. Consequent to the user's inputs, selections and/or responses on the one or more GUIs, the module 125 creates or generates the one or more montages in real-time (that is, on-the-fly while the EEG signals are being recorded by the plurality of electrodes 105) or offline (that is, by accessing EEG data stored in the at least one database 135).

In some embodiments, execution of sequences of programmatic instructions enables or causes the CPU to perform various functions and processes. In alternate embodiments, hard-wired circuitry may be used in place of, or in combination with, software instructions for implementation of the processes of systems and methods described in this application. Thus, the systems and methods described are not limited to any specific combination of hardware and software.

Figure 2:
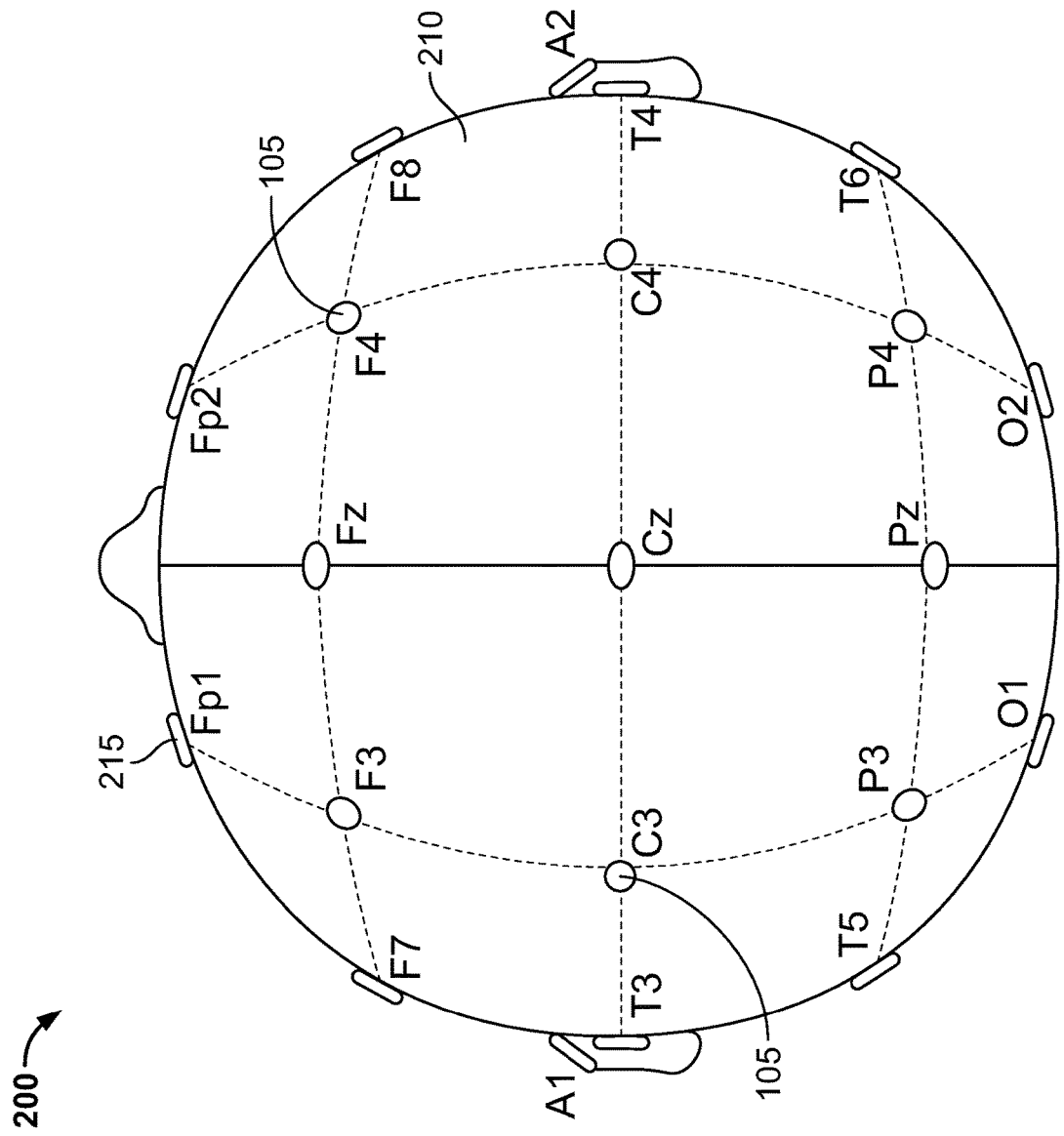
FIG. 2 illustrates the International 10-20 system of electrode placement on a patient's scalp, in accordance with some embodiments of the present specification.

It should be appreciated that the systems and methods of the present specification are particularly advantageous in high channel counts of electrodes requiring automated and customized montage creation. However, for the purposes of illustration the montage creation methods of the present specification are also described with reference to low channel counts of electrodes. For example, as shown in FIG. 2, the plurality of electrodes 105 may be spatially positioned on the patient's scalp 210 in accordance with the International 10-20 system 200. As known to persons of ordinary skill in the art, the system 200 uses the distance from the bridge of the nose (nasion) to the lowest point of the skull from the back of the head (normally indicated by a prominent bump—the inion) as a reference distance for a given person's head size. The electrodes 105 are then separated from each other either by 10% or 20% of this reference distance. Each electrode placement site has a letter to identify the lobe, or area of the brain it is reading from: Pre-frontal (N), Frontal (F), Temporal (T), Parietal (P), Occipital (0), and Central (C) and a numerical subscript representing position. The midline electrodes are marked with a subscript z, which stands for zero. The odd numbers are used as subscript for points over the left hemisphere and even numbers over the right.

In other embodiments, when greater resolution or granularity is required, the 10-20 system is extended where now the electrodes are separated by 10% of the reference distance (10-10). Further resolution of 5% separation (10-5) distances adds even more electrodes to the scalp. One of ordinary skill in the art would understand that the embodiments disclosed herein, wherein the electrodes are positioned on the patient's scalp, apply equally to data sets generated from a 10-20 system, a 10-10 system, a 10-5 system, or any other relative electrode distance that may be used.

Figure 3A:
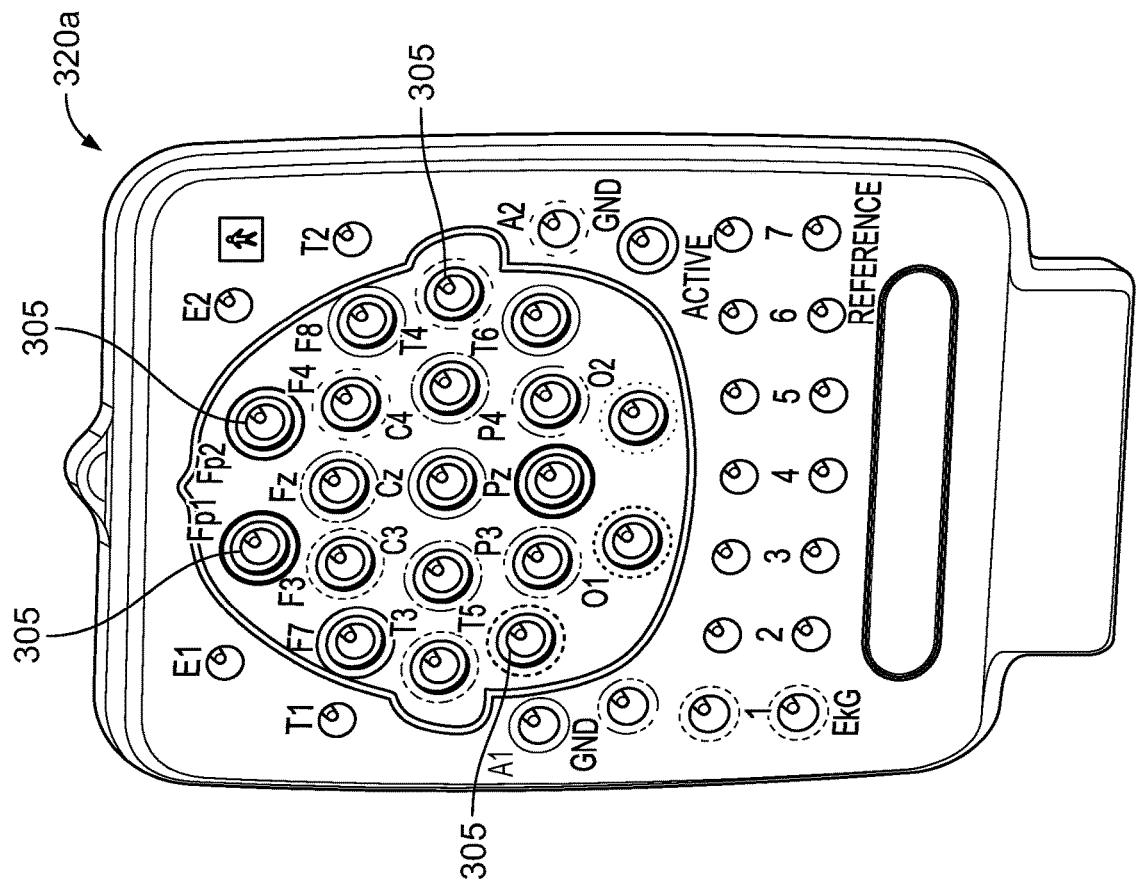
FIG. 3A is a perspective view of a multi-channel amplifier, in accordance with an embodiment of the present specification.

FIG. 3A shows a perspective view of an exemplary multi-channel amplifier 320a, in accordance with some embodiments of the present specification. The amplifier 320a has a plurality of electrode input channels or ports 305. In accordance with an embodiment, the plurality of input channels or ports 305 are arranged to replicate and correspond to the 10-20 system (system 200 of FIG. 2) of electrode placement on the patient's scalp, for example. The multi-channel amplifier 120 of FIG. 3A is used for neuromonitoring of patients using a plurality of electrodes positioned on their scalps.

Figure 3C:
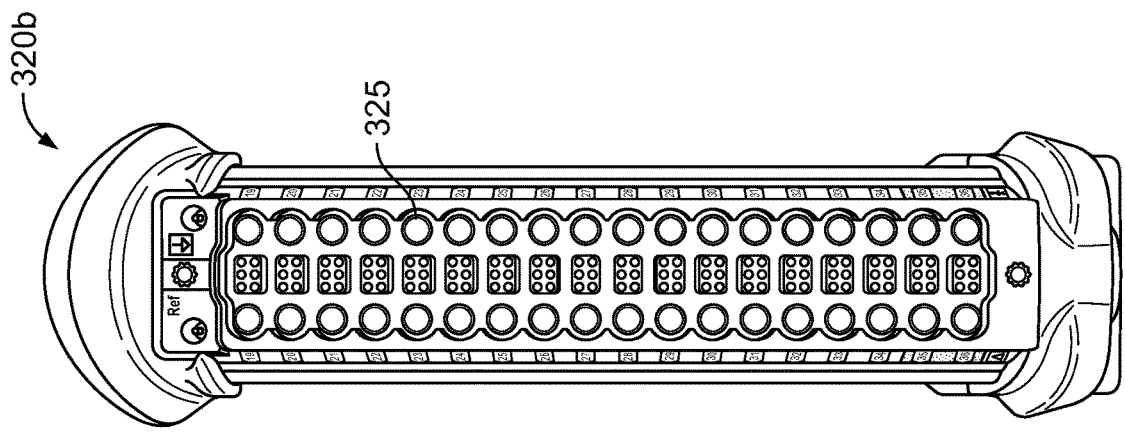
FIG. 3C is a side view of the multi-channel amplifier of FIG. 3B.
Figure 3B:
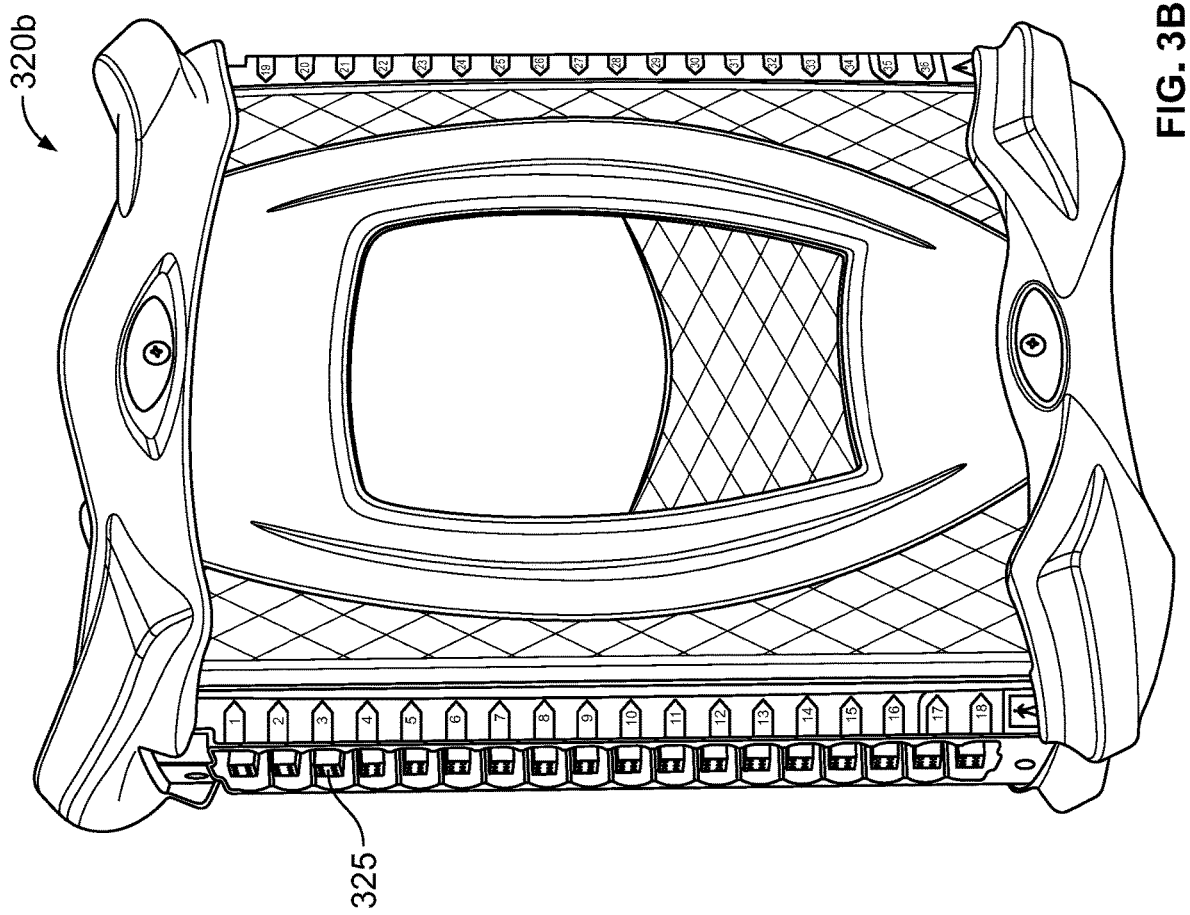
FIG. 3B is a perspective view of a multi-channel amplifier, in accordance with another embodiment of the present specification.

FIGS. 3B and 3C show perspective and side views, respectively, of another exemplary multi-channel amplifier 320b, in accordance with other embodiments of the present specification. The amplifier 320b has a plurality of electrode input channels or ports 325. In some embodiments, the amplifier 320b is configured to record up to 576 channels at an 8 kHz sampling rate. In some embodiments, the amplifier 320b includes an onboard battery and data storage to allow for patient mobility. In embodiments, the amplifier 320b is configured so that a user may select any input as ground on any input channel or port 325 and select any other input as the recording reference. Further, as discussed below, a user may create montages up to, and including, all electrodes with a single click on an associated GUI. In some embodiments, the amplifier 320 is configured to streamline electrode layout with automated input mapping.

The multi-channel amplifier 320b of FIGS. 3B and 3C may be used for high channel counts of electrodes positioned on a patient's scalp but is specialized for neuromonitoring of patients using a plurality of electrodes positioned intracranially. The electrodes may comprise grid, strip electrodes and/or depth electrodes and may be implanted via craniotomy or through small burr holes in the skull. The multi-channel amplifier 320b of FIGS. 3B and 3C may be used for ECoG and sEEG monitoring. In some embodiments, the multi-channel amplifier 320b of FIGS. 3B and 3C may be used for long term monitoring, for example, of epilepsy patients to monitor and map an epileptic brain to determine candidates for surgery. In some embodiments, referring back to FIG. 1, the automated montage creation module 125 of the EEG software 145 is configured to control integrated switch matrix stimulation. Additionally, in some embodiments, the software 145 allows a user to monitor multiple patients from one computer, control IP camera switching and functions, and simplify data review with trends and detection software. In some embodiments, all case settings, including montages, follow the patient record. In some embodiments, the software 145 includes a feature to automatically synchronize stimulus to response annotations.

Referring to FIGS. 1, 2, 3A, 3B and 3C in an embodiment, each of the plurality of electrodes 105 (FIG. 1) is in wired data communication with the corresponding input channel or port 305 (or 325) identifiable with the respective electrode. For example, an output wire or lead of the electrode Fp1 (referred to as element 215 in FIG. 2) is connected to the corresponding input channel 305 (FIG. 3A) on the amplifier 320a (or to the corresponding input channel 325 on the amplifier 320b), and so on. Thus, each recording electrode is uniquely identified and connected to the corresponding uniquely identified input channel or port 305. Consequently, each of the EEG signals acquired by the amplifier 120 is uniquely identified with the associated electrode 105.

Automated Montage Creation Module 125

Referring back to FIG. 1, the automated montage creation module 125 implements a plurality of programmatic instructions to enable a plurality of functions and features, as described in the paragraphs that follow. In some embodiments, the automated montage creation module 125 generates a GUI (Graphical User Interface) to display one or more two and/or three-dimensional topographical maps or views of the patient's head such that the plurality of electrodes and their relative positioning in the brain, on the brain and/or on the scalp are correspondingly identified and marked or displayed on the maps.

Figure 4A:
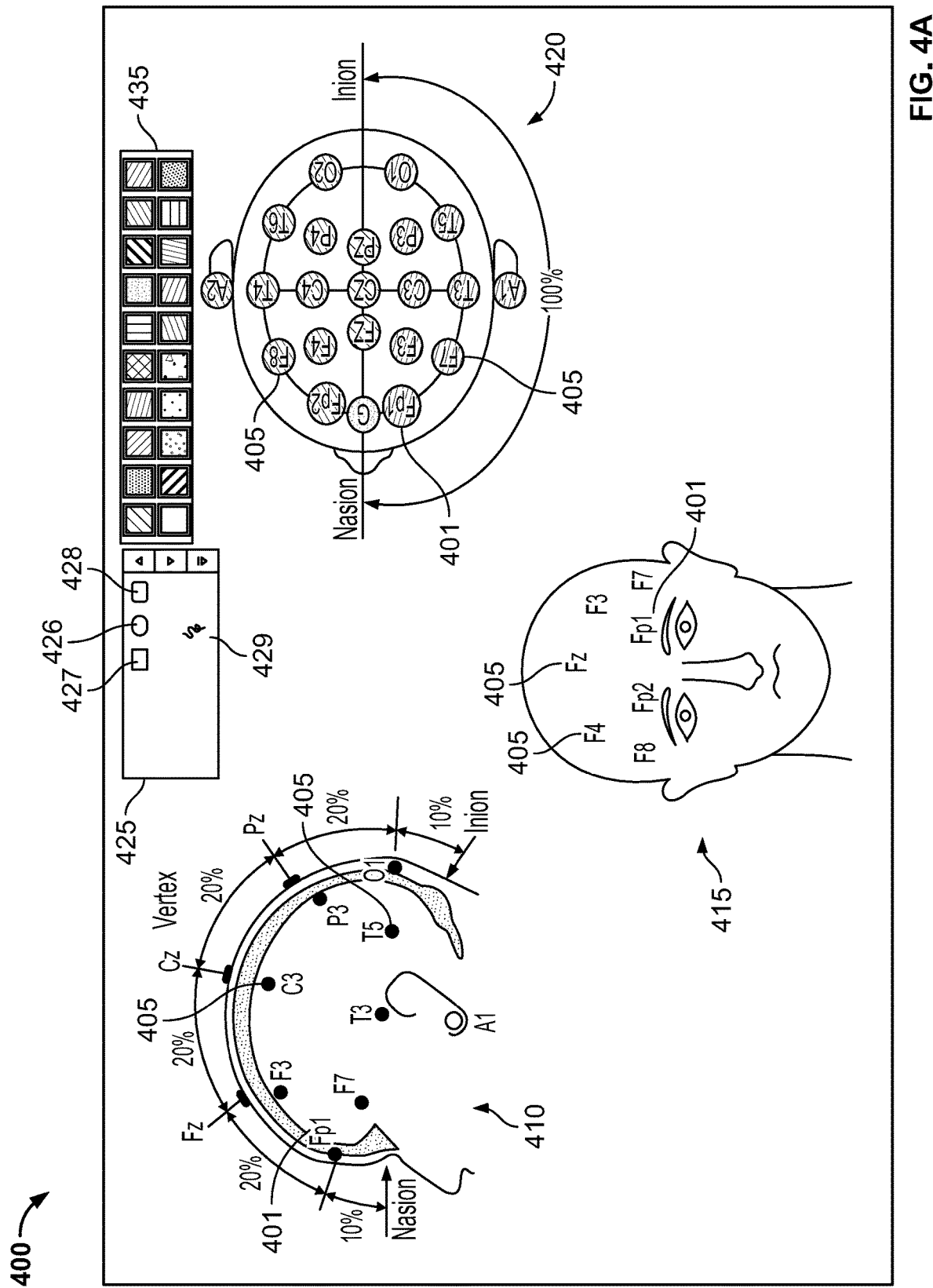
FIG. 4A is a depiction of an exemplary GUI screen illustrating a plurality of topographical maps of a patient's scalp and spatial positioning of a plurality of electrodes on the scalp, in accordance with some embodiments of the present specification.

FIG. 4A shows an exemplary GUI screen 400 illustrating a plurality of topographical maps of a patient's scalp and spatial positioning of a plurality of electrodes on the scalp, in accordance with some embodiments of the present specification. The screen 400 shows sagittal, coronal and top orthographic views 410, 415, 420 of the patient's scalp. It should be appreciated that the views 410, 415, 420 are exemplary and in no way limiting or binding. In embodiments where a large number of electrodes are used for monitoring and there is a high channel count (implanted electrodes plus possible scalp electrodes), there is a need for identifying which amplifier input corresponds to which electrode since the amplifier inputs may not be predefined or fixed. Further, naming electrodes may not be standardized as some electrodes (such as grid or strip electrodes or depth electrodes implanted via craniotomy or through small burr holes in the skull) may not correspond to a single anatomically standardized brain location. In such embodiments, for identifying graphical representations of electrodes against corresponding amplifier inputs, a special connector may be employed, such as the connector described in U.S. patent application Ser. No. 15/376,655, entitled "System and Method for High Density Electrode Management" and filed on Dec. 12, 2016, and in PCT Application No. PCT/US17/62559, entitled "System and Method for High Density Electrode Management" and filed on Nov. 20, 2017, both applications by the applicant of the present specification and both of which are herein incorporated by reference in their entirety.

The special connector described in said applications comprises a plurality of signal output pins which corresponds to a plurality of electrodes deployed on the body of the patient with the help of the connector. The plurality of electrodes are not directly connected with the input channels in the amplifier, rather the amplifier is coupled to the plurality of electrodes with the help of the special connectors which enable automatic detection of the electrodes, including their type and deployment location. The connectors are coupled to groups of a plurality of electrodes through one or more electrical leads. In some embodiments, the connectors are coupled to the groups of the plurality of electrodes through a wireless communication link. Each connector has a unique identity and is coupled to a plurality of electrodes which are included in the same group. When the electrodes are classified in the same group, it means their input signals are of the same type and their relative positions are fully defined. These electrodes are connected to the input terminals of the connector in a specific pre-defined order. A connector having 'n' channels can accommodate an electrode group with maximum number of n electrodes wherein n is any natural number. In commercial applications, the value of n is usually 4, 6, 8, 10, 12 and 16, such that the corresponding number of electrodes can be coupled to a single connector.

Each connector comprises a specific identification (ID) output pin which is used to establish the unique identity (ID) of the connector. A receiving socket corresponding to the connector comprises a bank of signal input points or sockets which are configured to receive the signal output pins of the connector. Usually, a receiving socket comprises enough input points to receive multiple connectors. In practical applications involving high density electrodes, the number of input points is over 200. The receiving socket is coupled to a control unit/amplifier which is used to control the entire system. The receiving socket may comprise a separate ID input socket which is configured to receive the ID output pin of the connector. The connector is inserted in the receiving socket such that the ID output pin is received in the ID input socket and the signal output pins are received in a subset of signal input sockets.

Once the identity of the connector is established, the type and location of all the electrodes coupled to the connector irrespective of the set of input sockets in which the connector is inserted may be identified. Once the electrodes are identified, the control unit coupled to the receiving socket reconfigures the detection system to automatically correlate, associate, assign or map each electrode with its corresponding input channel.

Each of the connectors has a unique ID (identity). This identification information is stored in the connector and is accessible to the system from its identification (ID) output pin. The ID information specifies the type and relative location of each electrode in the connector. In embodiments, the ID field comprises a GUID (Globally Unique Identifier) which is a standard format comprising 128-bit data and is used as an identifier in the computer software. It may also contain other device specific information about the attached device. Once a GUID is assigned, each input can be uniquely identified thereafter. In embodiments, the GUID data is stored in an inbuilt memory device in the connector and, optionally, the memory device is an EPROM storage device.

In some embodiments, a user may set up the graphical representation, such as shown in FIG. 4A by using the special connector described above. Typically, each sub-contact in a multi-contact electrode is numbered and the electrodes have a color coded tail with multiple contact points, each with a known correlation to numbered sites on the implanted multi-contact electrode. In order to set up the graphical representation and enable detection, each of the electrode tails is connected to amplifier inputs via the special connector described above. A control unit coupled with the connector and the amplifier may also provide a graphical representation of the connector and its position on the amplifier and, in cases where the electrodes have been manually connected to the connector and the amplifier, the user is required to associate the graphical representation of the multi-contact electrode to the graphical representation of the amplifier input. For example, in some embodiments, a user uses an input device, such as a mouse, to click and drag a cursor on a GUI to or over specific a specific electrode or electrodes to select the electrode or electrodes for a montage. In another example, in other embodiments, a user touches an area on a touchscreen of a GUI to click and drag a selection area to or over specific a specific electrode or electrodes to select the electrode or electrodes for a montage.

In some embodiments, each of the electrodes 105 (FIG. 1, 2) is correspondingly identified and marked/displayed as an electrode channel 405 on each of the views 410, 415, 420 by using the connector and corresponding control unit as described above. For example, the actual electrode position Fp1 (referenced as 215) on the scalp in FIG. 2 is correspondingly identified and marked as Fp1 (referenced as 401) on the views 410, 415, 420 on the screen 400. Similarly, in high channel counts of electrodes (such as those used with amplifier 320b of FIGS. 3B and 3C), each of the electrode 105 is uniquely identified and marked/displayed as an electrode channel 405 on each of the views 410, 415, 420 by using the connector.

In some embodiments, when executed by the processor of the computing device 140, the automated montage creation module 125 generates and transmits data to the display 130 that is indicative of a montage selection toolbar. The montage selection toolbar enables a user to use a drawing loop to indicate selection of one or more electrode combinations or montages. Additionally or alternatively, the user may point and click his mouse at an electrode channel or the user may point, click and drag the mouse between two electrode channels/contacts to indicate selection of one or more electrodes combinations or montages. Montages (or combinations of electrodes) provide a picture of the spatial distribution of the EEG across the patient's cortex. Accordingly, a montage is an electrical map obtained from a spatial array of recording electrodes and refers to a particular combination of electrodes examined at a particular point in time.

Referring back to FIG. 4A, a montage selection toolbar 425 enables the user to pick a selection drawing tool or loop from a plurality of exemplary drawing tool or loop shapes such as, but not limited to, circular/oval 426, rectangular with sharp corners 427, rectangular with rounded corners 428 and free form 429. In various embodiments, the loop shapes may be square, spherical, or cylindrical. In various embodiments, the user may click from identification to identification in a 'connect the dots' or 'dot to dot' manner to select identifications. In various embodiments, an entire strip, grid, or depth electrode may be selected by clicking and dragging a cursor over or 'looping' the electrode. In some embodiments, the user may click on a strip, grid or depth electrode body (instead of on a specific identifier electrode site) to select an entirety of the strip, grid or depth electrode. In some embodiments, the user may press the 'shift' key (on his keyboard) and click to select multiple electrode collections. An optional color palette 435 allows the user to select different colors for the selection loop.

Figure 4B:
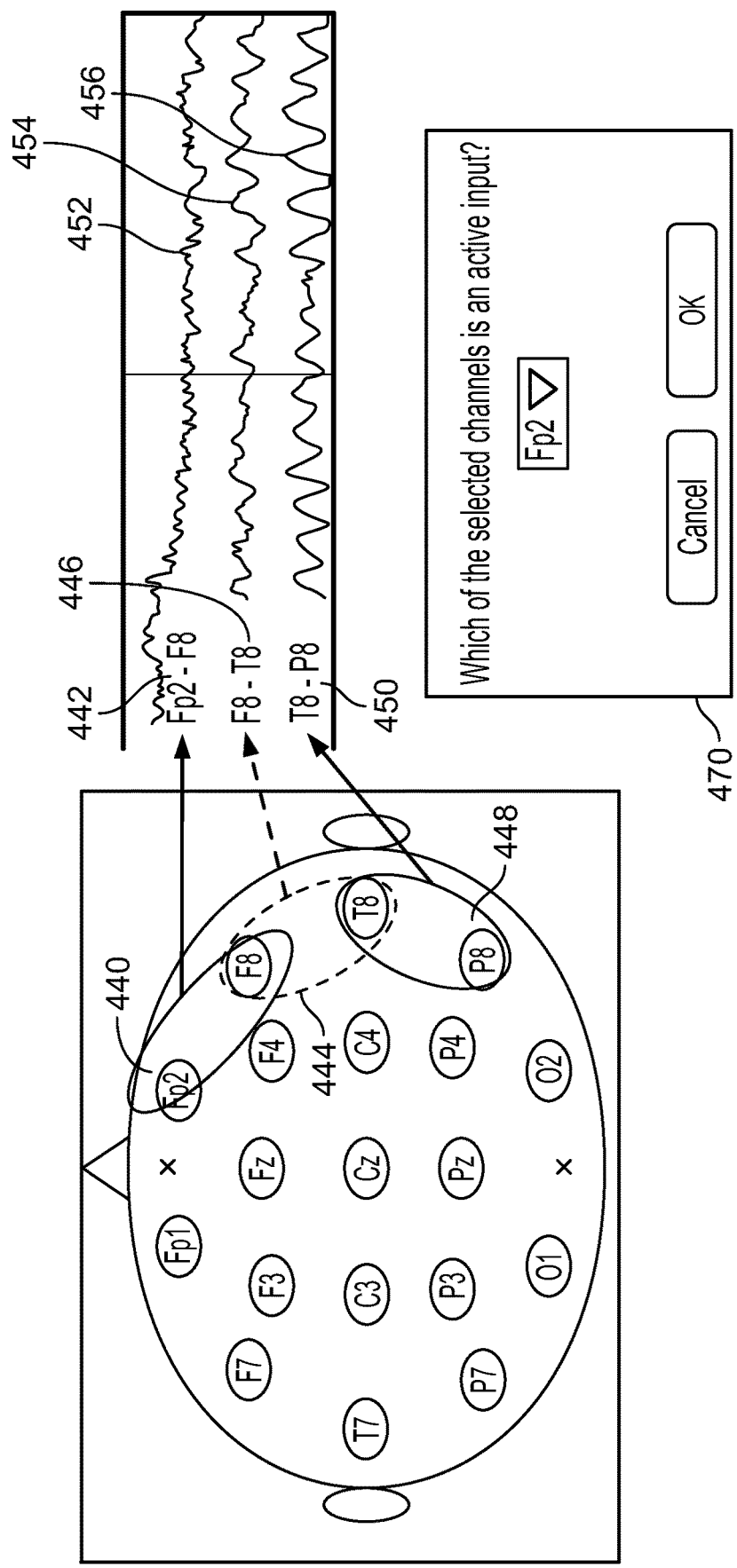
FIG. 4B is a depiction of various exemplary GUIs that demonstrate the use of drawing loops to select a plurality of exemplary bipolar montages, in accordance with some embodiments of the present specification.

FIG. 4B shows GUIs demonstrating use of drawing loops to select a plurality of exemplary bipolar montages, in accordance with some embodiments of the present specification. Bipolar montages are based on the principle of comparing a single EEG electrode tracing to its adjacent neighboring electrode. In an embodiment, the user may use a selection drawing loop such as, for example, the circular/oval loop (loop 426 of FIG. 4A) to select a plurality of anterior-posterior bipolar montages. In embodiments, when the user draws a loop around two adjacent electrode channels, the module 125 (FIG. 1) senses selection of two electrode channels and concludes that the user would like to create bipolar montages. In some embodiments, the module 125 senses the electrode channels as being selected if the pixel coordinates of the electrode channels lie within and/or touch the pixel coordinates of the drawn loop.

Thus, the user may draw a first loop 440 to enclose Fp2 and F8 electrodes to indicate formation of a first bipolar montage 442, a second loop 444 to enclose F8 and T8 electrodes to indicate formation of a second bipolar montage 446 and a third loop 448 to enclose T8 and P8 electrodes to indicate formation of a third bipolar montage 450 and so on. In embodiments, for each indicated montage the module 125 may prompt the user to specify active and reference electrode channels—that is, a "direction" of the montage. As an illustration, the module 125 displays a dialog box 470 when the user draws the first loop 440. The dialog box 470 asks the user to select the active electrode from the two enclosed electrodes Fp2 and F8. When the user selects, for example, Fp2 as the active electrode the other electrode F8 is automatically designated as a reference electrode. Similar dialog boxes may be presented to the user for each of the second and third loops 444, 448.

The automated montage creation module 125 acquires or accesses EEG signals corresponding to the electrodes associated with the one or more montages, selected by the user using the montage selection toolbar 425. Referring back to FIG. 1, in some embodiments, the automated montage creation module 125 accesses EEG signals acquired using the plurality of electrodes and stored in the database 135 of the EEG system 100. In other words, the module 125 accesses offline or pre-stored EEG signals in order to create montages. In some embodiments, the automated montage creation module 125 acquires EEG signals in real time while the EEG signals are being recorded using the plurality of electrodes 105. As discussed with reference to FIGS. 1, 2, 3A, and 3B each recording electrode 105 is uniquely identified and connected to the corresponding uniquely identified input channel or port 305 of the amplifier 120. Consequently, each of the EEG signals acquired by the amplifier 120 is uniquely identified with the associated electrode.

In some embodiments, the automated montage creation module 125 creates or generates the one or more montages as selected by the user on the GUI. In some embodiments, the module 125 uses pre-stored EEG signals to create or generate the one or montages as a consequence of the user's selection. In some embodiments, the module 125 uses real time EEG signals to create or generate the one or more montages, on the fly, as a consequence of the user's selection. It should be appreciated that for montage creation, EEG channel names are automatically derived from the letter (that represents the underlying area or lobe of the brain) and numerical subscript (representing position on the underlying area of lobe of the brain) of the electrodes.

Figure 4C:
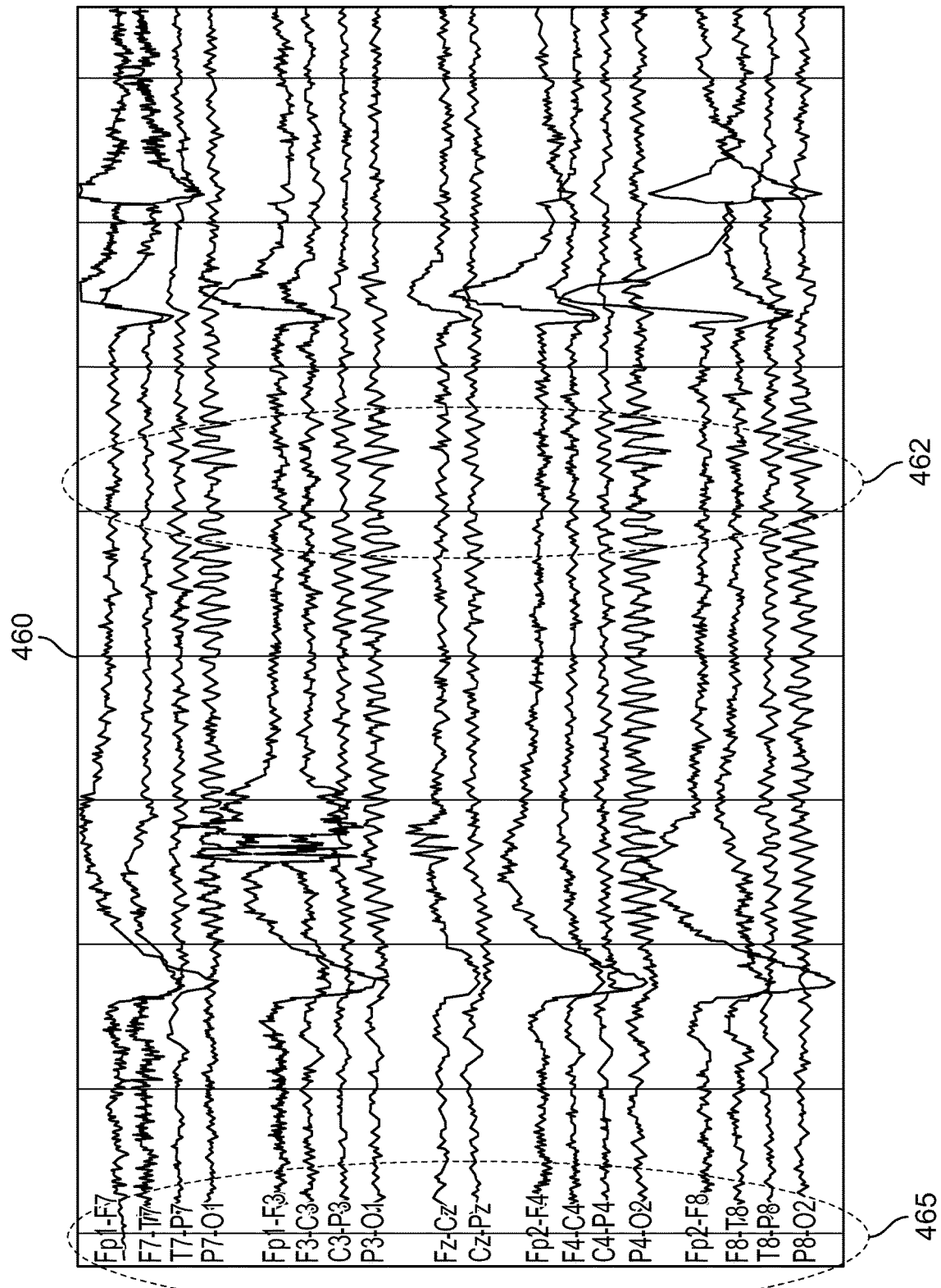
FIG. 4C is an EEG report comprising EEG tracings corresponding to a plurality of bipolar montages, in accordance with some embodiments of the present specification.

In some embodiments, the automated montage creation module 125 displays at least one EEG report that shows EEG traces corresponding to the one or more montages created or generated as a result of the user's selection. Referring back to FIG. 4B, as a result of the user's selection to form first, second and third bipolar montages 442, 446, 450, corresponding first, second and third EEG tracings 452, 454, 456 are displayed. FIG. 4C shows an exemplary EEG report 460 comprising a plurality of EEG tracings 462 corresponding to a plurality of bipolar montages 465 selected by the user using the drawing loop and, consequently, automatically generated by the module 125.

In some embodiments, the user may use his mouse to point and click on a first electrode contact and then drag the mouse pointer to release at a second electrode contact. As a result of the user pointing, clicking, dragging and releasing the mouse pointer between two electrodes, the module 125 (FIG. 1) senses selection of two electrode channels and concludes that the user would like to configure the first and second electrodes as a bipolar montage. In some embodiments, clicking and dragging the mouse between the first and second electrodes may also result in drawing an arrow between the first electrode used as the active input and the second electrode used as the reference input. In some embodiments, a head of the arrow is at the reference input contact/electrode and is indicative of the "direction" of the bipolar montage.

Figure 5A:
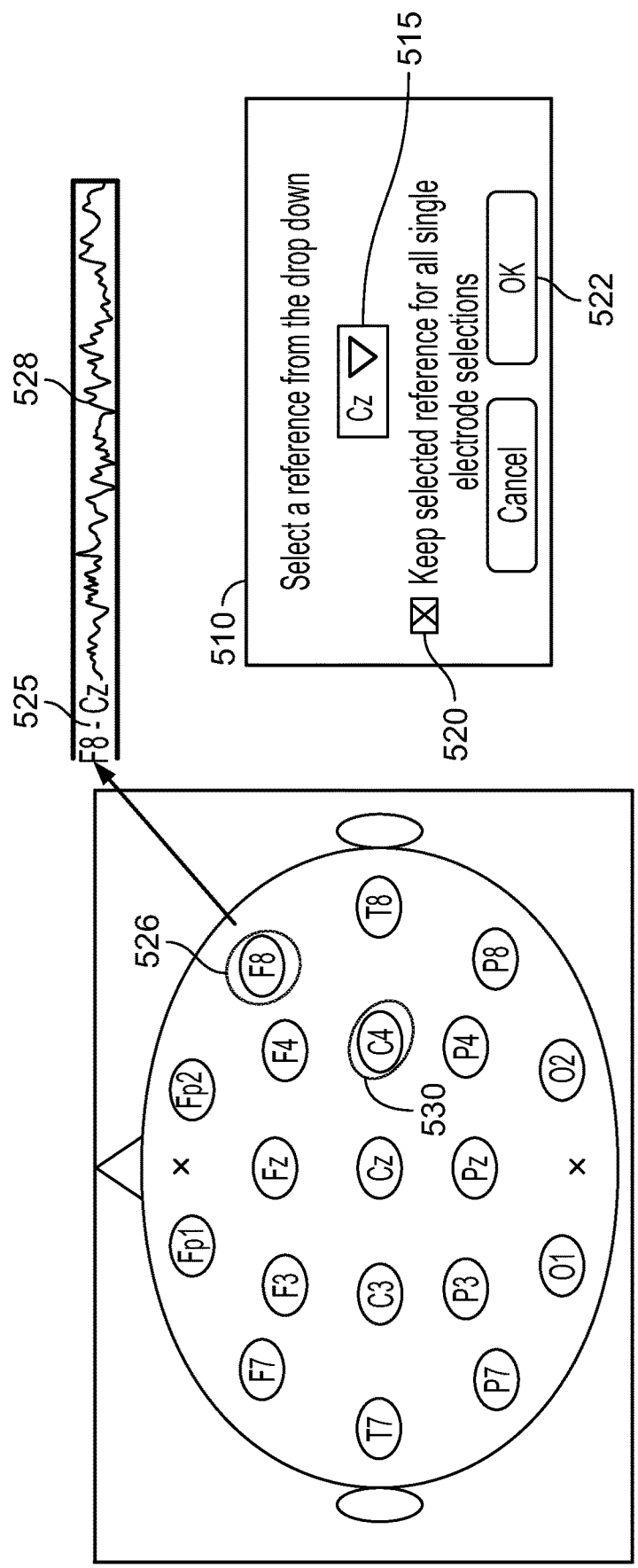
FIG. 5A is a depiction of various exemplary GUIs demonstrating use of drawing loops to select a plurality of exemplary referential montages, in accordance with some embodiments of the present specification.

In some embodiments, a plurality of referential montages (or common-reference montages) may be indicated by the user via selection of singular electrodes using the drawing loop. These referential montages are then generated or created automatically by the module 125. For referential montages, signals at each of the plurality of electrodes are compared to a single common reference. FIG. 5A shows GUIs demonstrating use of drawing loops to select a plurality of exemplary referential montages, in accordance with some embodiments of the present specification. In an embodiment, the user uses a first selection loop 526 such as, for example, a circular/oval loop to select a first electrode such as, for example, F8. The module 125 senses that the user has selected a single electrode (that is, F8 in this example) and therefore concludes that the user would like to form a referential montage. Consequently, the module 125 displays a dialog box 510 to the user asking the user to select a reference for the selected first electrode F8. In an embodiment, the user selects Cz (for example) as a reference for the first electrode F8 from a drop down list 515 of references. In some embodiments, the dialog box 510 provides the user with an option 520 to set the selected reference, that is Cz in this case, as a default reference for all subsequent singular electrode selections for montage formation. On clicking the ok button 522, the module 125 generates or creates a first referential montage 525 and displays a first EEG tracing 528 corresponding to the first referential montage 525. Also, when the user draws a second selection loop 530 around a second electrode C4, for example, the module 125 generates a second referential montage C4-Cz (FIG. 5B) and displays a second EEG tracing (FIG. 5B) corresponding to the second referential montage.

In some embodiments, the user may use his mouse to point, click and release on an electrode—as a result of which, the module 125 (FIG. 1) senses selection of a single electrode channel and concludes that the user would like to configure the electrode as part of a referential montage. In some embodiments, an electrode contact that has a referential channel in the montage is highlighted either in a unique color or any other indication such as, but not limited to, a circle around it.

Figure 5B:
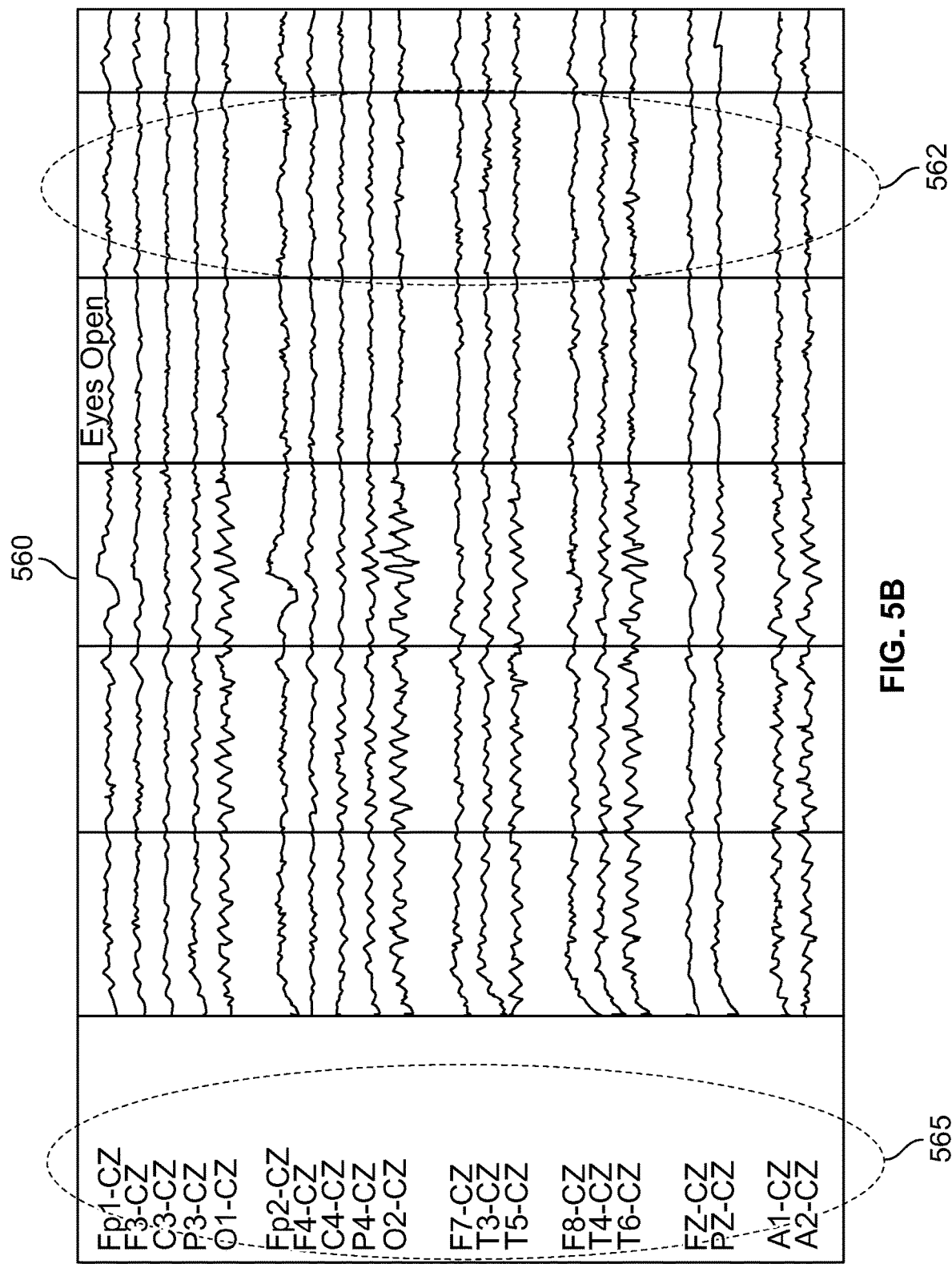
FIG. 5B is an EEG report comprising EEG tracings corresponding to a plurality of referential montages, in accordance with some embodiments of the present specification.

FIG. 5B shows an EEG report 560 comprising a plurality of EEG tracings 562 corresponding to a plurality of referential montages 565 selected by the user using the drawing loop and automatically generated by the module 125.

In some embodiments, the user clicks the mouse in a region of the GUI that does not display an electrode and thereafter drags the mouse pointer to begin drawing a selection loop. When the mouse is released, all electrode contacts contained in or touched by the loop are automatically added to the montage—by the module 125 (FIG. 1). At this point the user is prompted to select referential or bipolar for the type of channels to be added. This looping mode of selection is efficient since the user may simply draw a loop around, for example, 64 input channels of an 8×8 grid electrode (for example) and thereafter choose whether the selected channels should be referential or bipolar. Comparatively, in the mouse clicking mode of selection the user would have to click 64 times in order to add all channels for a montage.

For bipolar traces, the user selects a 'direction' to define which channels will be active and which channel(s) will be reference. In some embodiments, a system setting of 'ascending' will automatically assign a lower numbered channel as the active and the next highest numbered channel as the reference. Alternatively, a system setting of 'descending' will assign the higher numbered channel as the active and the next lower numbered channel as the reference. Further, a system setting of 'ascending across' will assign the lower numbered channel as the active and the next highest channel that is in the same column as the active channel as the reference. For example, in an 8×8 grid, channel 1 is the active and channel 9 is the reference. Still further, a system setting of 'descending across' is the reverse of 'ascending across' so that channel 9 is the active and channel 1 is the reference (from previous example). In some embodiments, the system settings indicative of the 'direction' are available by default, which may be modified by the user.

Figure 6A:
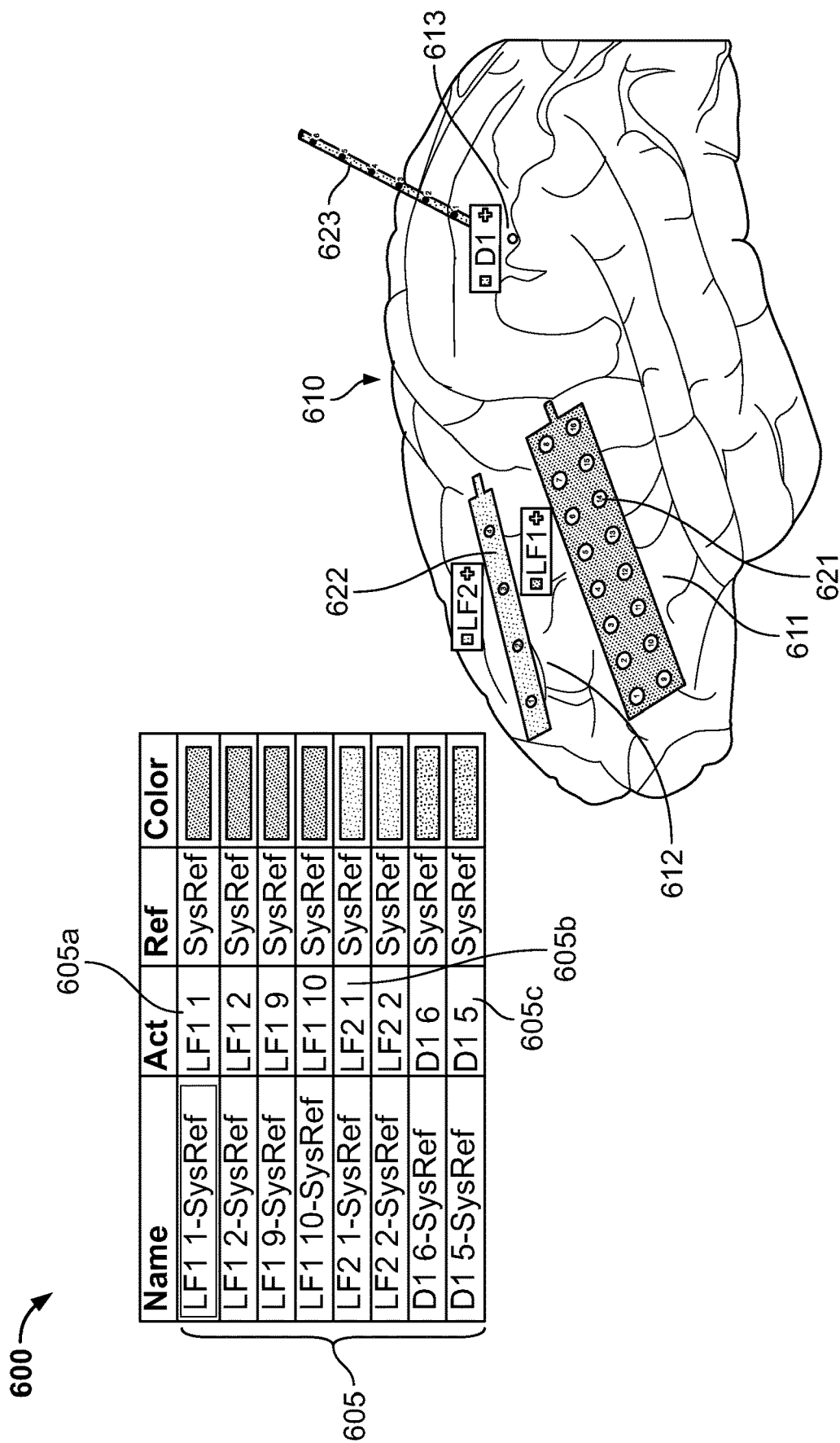
FIG. 6A is an illustration of an exemplary GUI showing a plurality of montages and a patient brain showing the locations of sections of the brain associated with the montages, in accordance with some embodiments of the present specification.

In some embodiments, where multi-contact electrodes are used, a user may set up a graphical representation of a montage, such as shown in FIG. 6A. FIG. 6A is an illustration of an exemplary GUI 600 depicting a plurality of montages 605 and a patient brain 610 depicting the locations of sections 611, 612, 613 of the brain 610 associated with the montages, in accordance with some embodiments of the present specification. In some embodiments, the montages are color coded for reference. For example, in one embodiment, montage LF1 605*a* is coded blue and refers to section 611 of the brain 610 and associated grid electrodes 621, montage LF2 605*b* is coded red and refers to section 612 of the brain 610 and associated strip electrodes 622 while montage D1 605*c* is coded green and refers to section 613 of the brain 610 and associated depth electrodes 623.

Figure 6B:
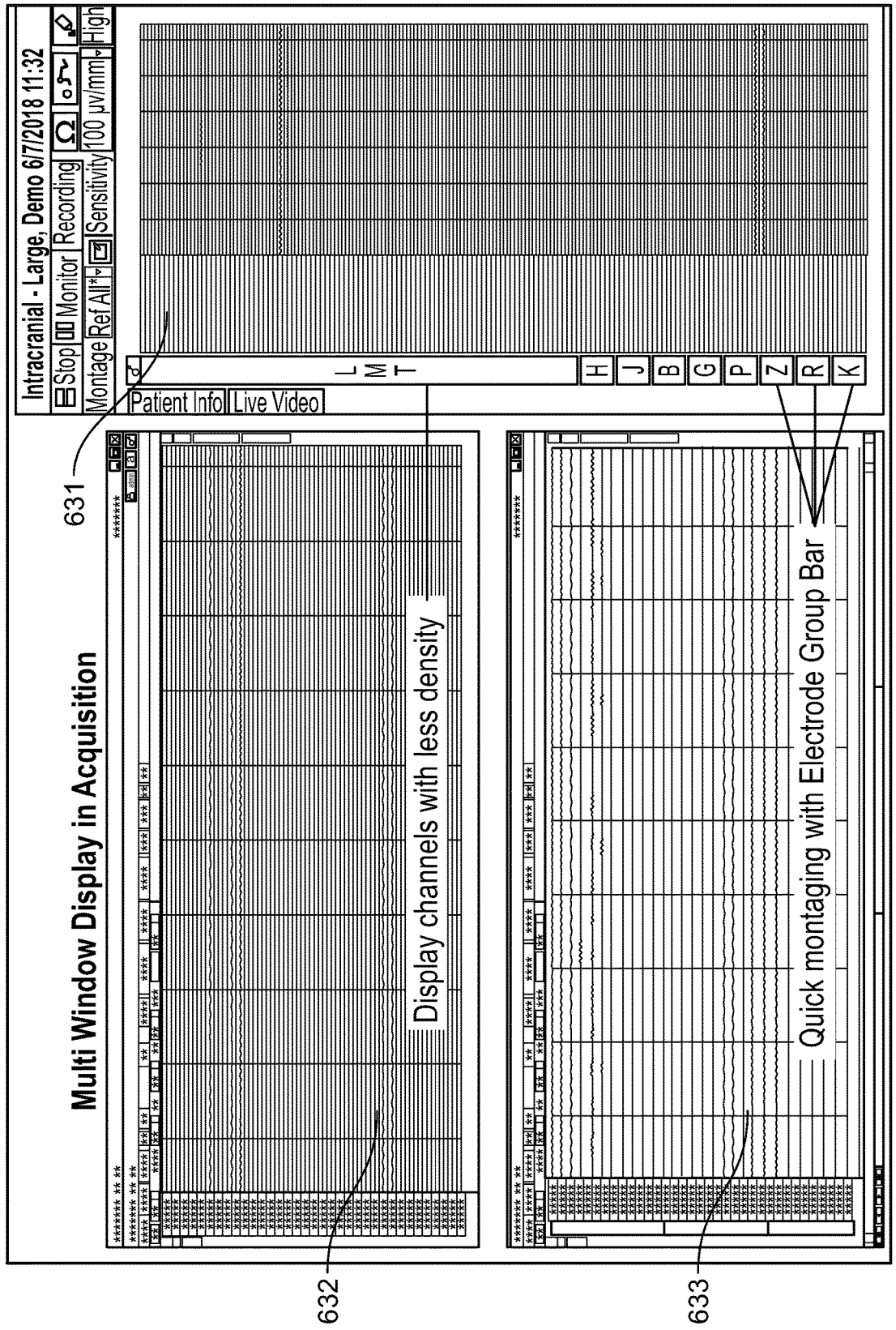
FIG. 6B is a depiction of a multi-window GUI display in accordance with some embodiments of the present specification.

FIG. 6B is a depiction of a multi-window GUI display 630 in accordance with some embodiments of the present specification. The multi-window GUI display 630 may be used with the EEG systems of the present specification and provides several sub-windows to enhance monitoring during acquisition. In some embodiments, the multi-window GUI display 630 includes a main window 631 and at least a first sub-window 632 and a second sub-window 633. In some embodiments, the first sub-window 632 is configured to display a specific subset of channels, with less density, of the group of channels displayed in the main window 631. In some embodiments, the second sub-window 633 is configured to allow for quick montaging with electrode group bars.

Figure 6C:
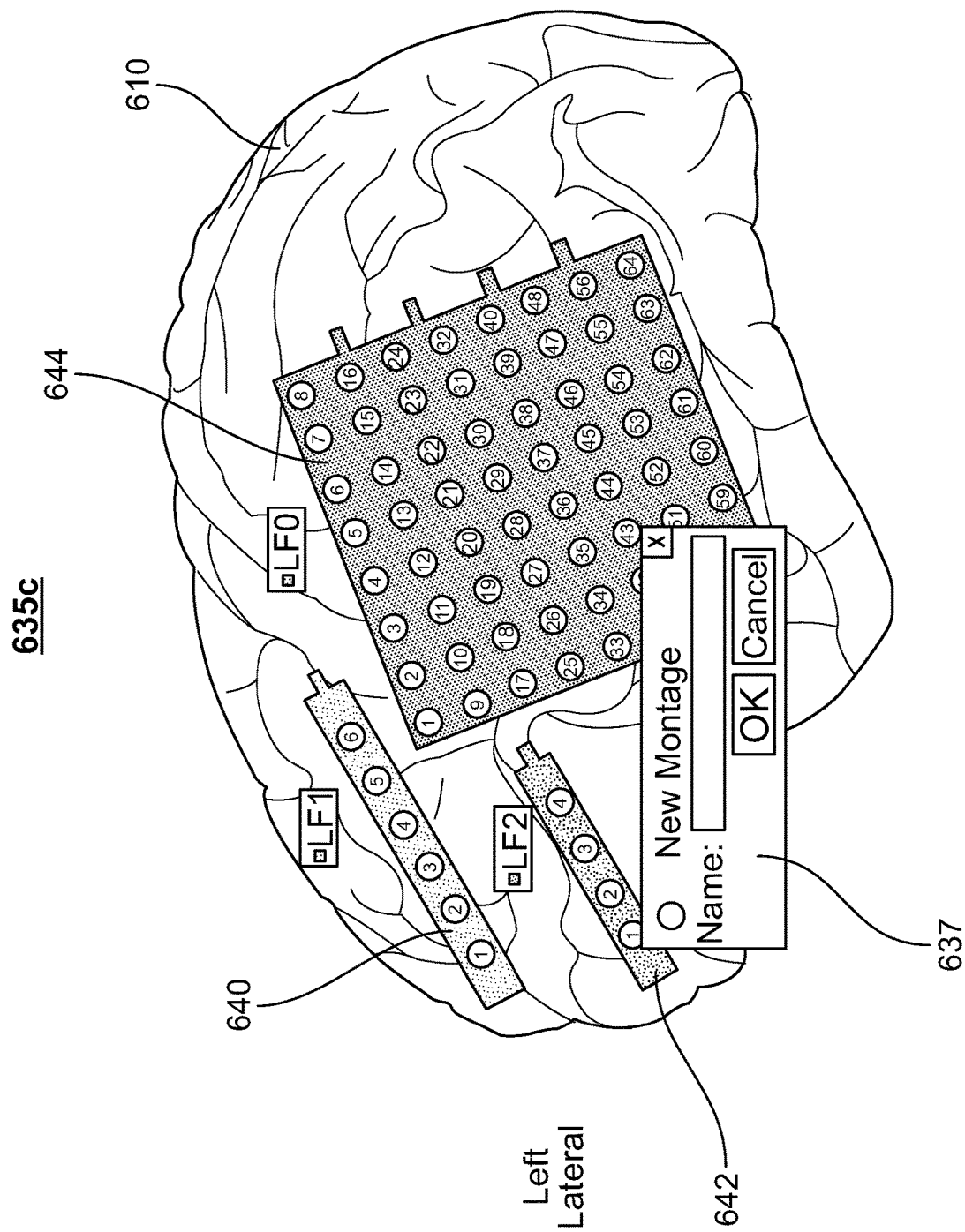
FIG. 6C shows a first GUI depicting a patient brain along with a dialog box to generate a new montage, in accordance with some embodiments of the present specification.
Figure 6D:
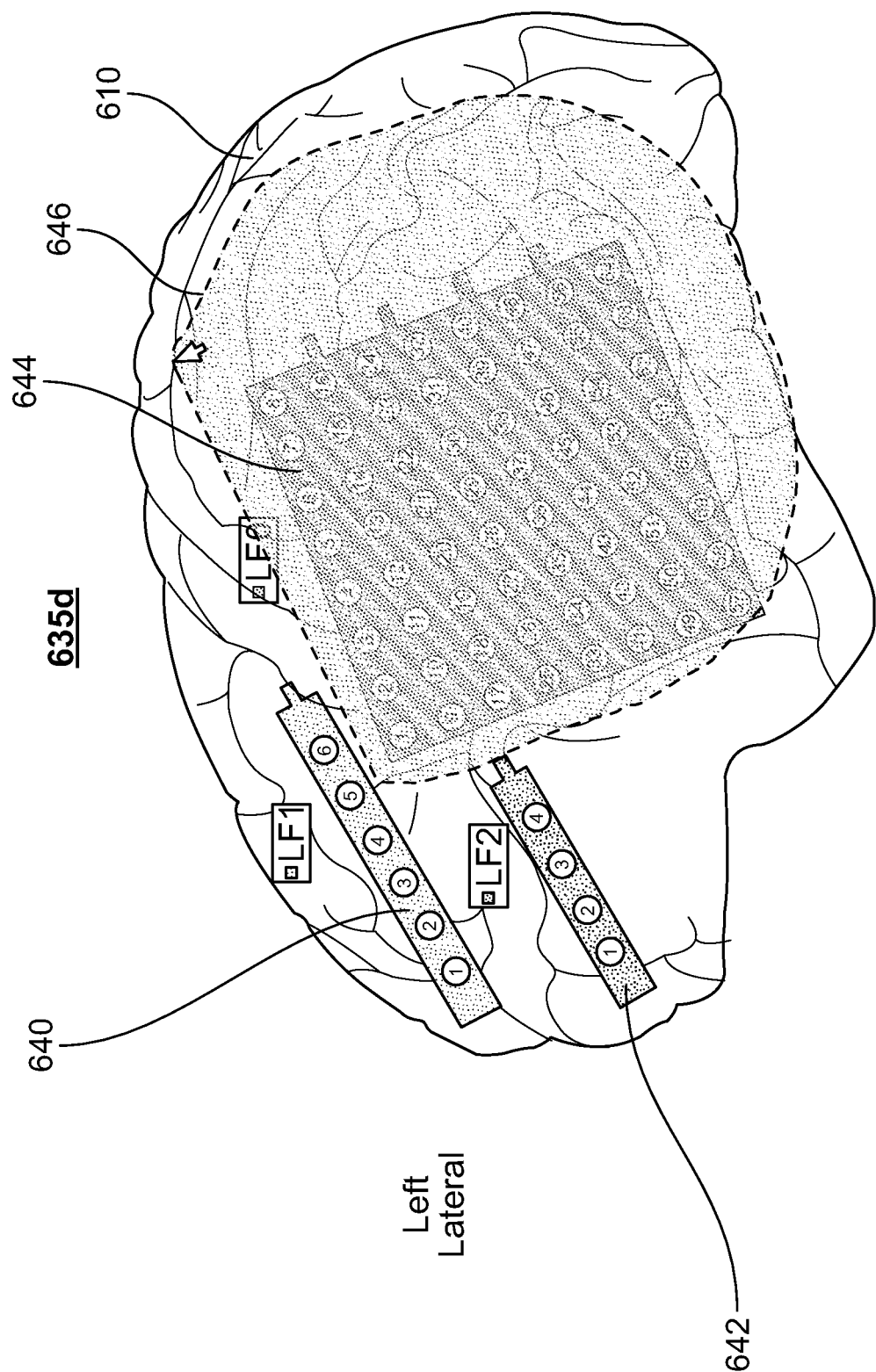
FIG. 6D shows a second GUI depicting selection of all channels of a grid electrode using a drawn area or loop encompassing the grid electrode, in accordance with some embodiments of the present specification.
Figure 6E:
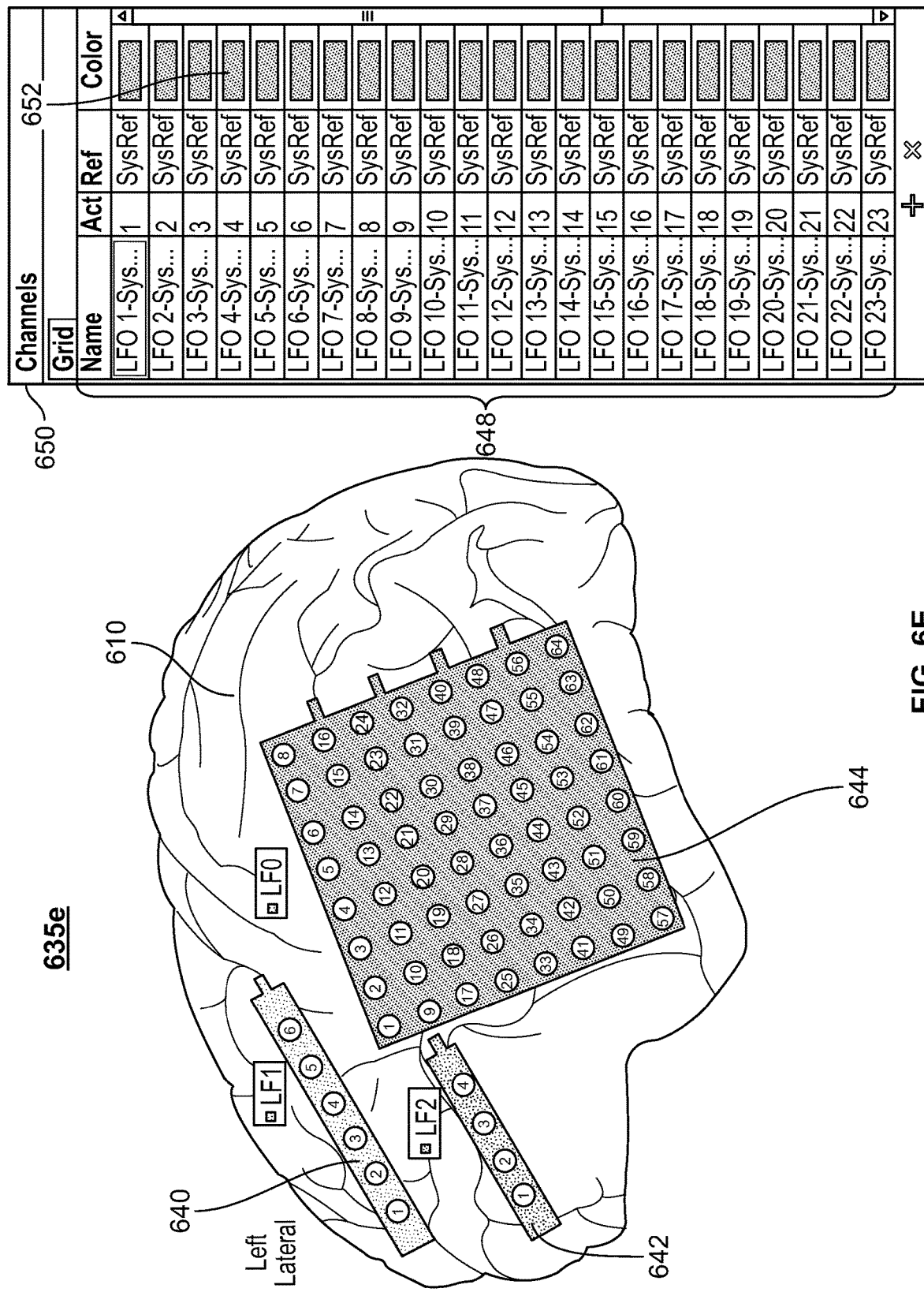
FIG. 6E shows a third GUI illustrating a plurality of referential montages created as a result of selection of all channels of the grid electrode on FIG. 6D, in accordance with some embodiments of the present specification.

FIG. 6C shows a first GUI 635*c* depicting a patient brain 610 along with a dialog box 637 to generate a new montage, in accordance with some embodiments of the present specification. The GUI 635*c* shows positioning of first and second strip electrodes 640, 642 (identified as LF1 and LF2, respectively) along with an 8×8 grid electrode 644 (identified as LFO). In an embodiment, the user may input "LFO-Ref" in the dialog box 637 indicating that he would like to create referential montages for the grid electrode 644 (LFO). Thereafter, as shown in a second GUI 635*d* of FIG. 6D, in embodiments, the user may click and drag his mouse to draw an area or a loop 646 (that in one embodiment is a free form drawing) to encompass the grid electrode 644, thereby simultaneously selecting all 64 channels of the grid electrode 644 for the new montage. It should be appreciated that each of the 64 channels is uniquely identified with alphanumeric notation ranging from LFO 1 to LFO 64. Consequently, 64 channels are automatically and simultaneously grouped into a new montage. The third GUI 635*e* of FIG. 6E shows the 64 montage channels 648 listed in a window 650. In embodiments, the montage channels 648 are associated by color codes 652.

In some embodiments, the module 125 (FIG. 1) provides the user a feature to automatically create montages that include, for example, "all depth electrodes", "all subdural (strip, grid) electrodes", "all electrodes" (that is, all depth and subdural electrodes) or other customized groups of electrodes based on particular characteristics of placement location or electrode type. FIG. 6F is a GUI 660*f* to enable a user to select one or more of a plurality of auto-generated montage settings 665, in accordance with some embodiments of the present specification. The user can interact with the GUI 660*f* to have montages automatically created as electrodes are added or removed. While implant cases rarely (if ever) have the same electrode configuration from patient to patient, the montages used often contain the same types of channels and patterns. Using the settings 665, the user can simply add electrodes and have the needed general montages created automatically saving a significant amount of time and effort.

As an illustration, the plurality of auto-generated montage settings 665 of GUI 660*f* have been shown for implant electrodes (grid, strip and depth) only since those types of cases rarely have the same electrode configuration as opposed to scalp recordings which often have the same electrode configuration. Accordingly, with reference to the implant electrodes, the plurality of auto-generated montage settings 665 includes:

All Referential 665*a*—Selection of this setting automatically creates a montage containing referential channels for every electrode contact.

All Bipolar 665*b*—Selection of this setting automatically creates a montage containing bipolar channels (ascending) for every electrode contact.

Subdural Referential 665*c*—This montage is generated only if strip and/or grid electrodes are present. Selection of this setting automatically creates a montage containing referential channels for all contacts of every strip and grid electrode.

Subdural Bipolar 665*d*—This montage is generated only if strip and/or grid electrodes are present. Selection of this setting automatically creates a montage containing bipolar channels (ascending) for all contacts of every strip and grid electrode.

Depth Referential 665*e*—This montage is generated only if depth electrodes are present. Selection of this setting automatically creates a montage containing referential channels for all contacts of every depth electrode.

Depth Bipolar 665*f*—This montage is generated only if depth electrodes are present. Selection of this setting automatically creates a montage containing bipolar channels (ascending) for all contacts of every depth electrode.

Mixed 665*g*—This montage is generated only if depth and strip and/or grid electrodes are present. Selection of this setting automatically creates a montage containing referential channels for all contacts of every strip and grid electrode and bipolar channels (ascending) for all contacts of every depth electrode.

Sparse Referential 665*h*—This montage is generated only if the total electrode contact count exceeds 100. Selection of this setting automatically creates a montage containing between 50 and 100 referential channels from each electrode.

Add Spaces between Electrodes 665*i*—Selection of this setting automatically adds a blank space between the channels of each electrode. For example, if electrode A has 8 channels and electrode B has 10 channels, a space will be added between A8 and B1 as a result of selection of this setting.

Figure 6G:
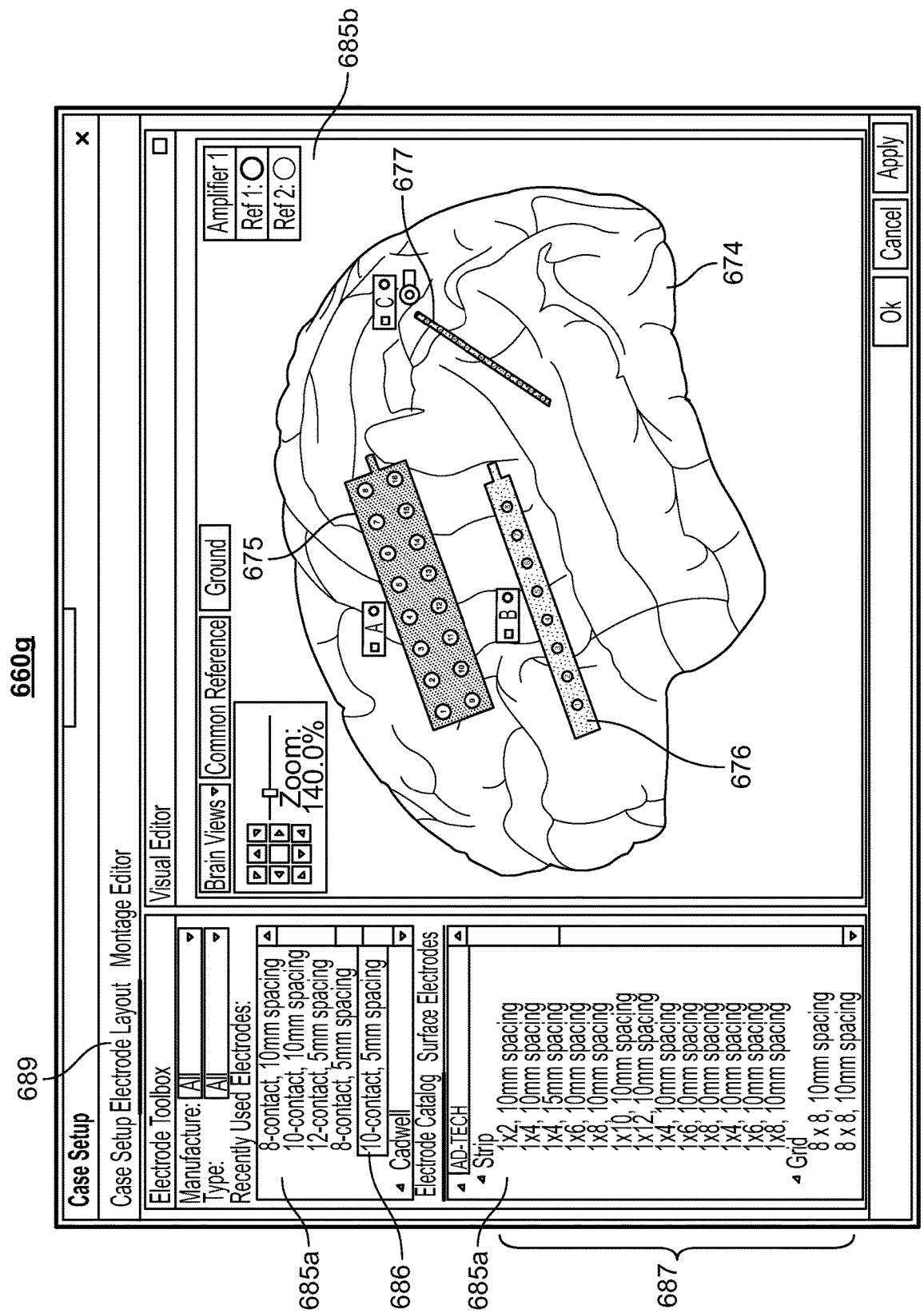
FIG. 6G shows another GUI to enable the user to configure and add electrodes, in accordance with some embodiments of the present specification.

FIG. 6G shows a GUI 660*g* to enable the user to configure and add electrodes, in accordance with some embodiments of the present specification. Upon selecting an electrode layout tab 689, the user navigates to a first window 685*a* displaying a plurality of recently used electrodes (with associated spacing between the electrode channels), of which a 10 contact 5 mm spacing electrode 686 is shown as selected by the user. Also displayed in the first window 685*a* is a catalog 687 of a plurality of strip and grid electrodes (with associated spacing between the electrode channels). A second window 685*b* displays a view of a patient's brain 674 with positioning of an 8×8 contacts grid electrode 675, an 8 contacts strip electrode 676 and a 10 contacts depth electrode 677.

Figure 6H:
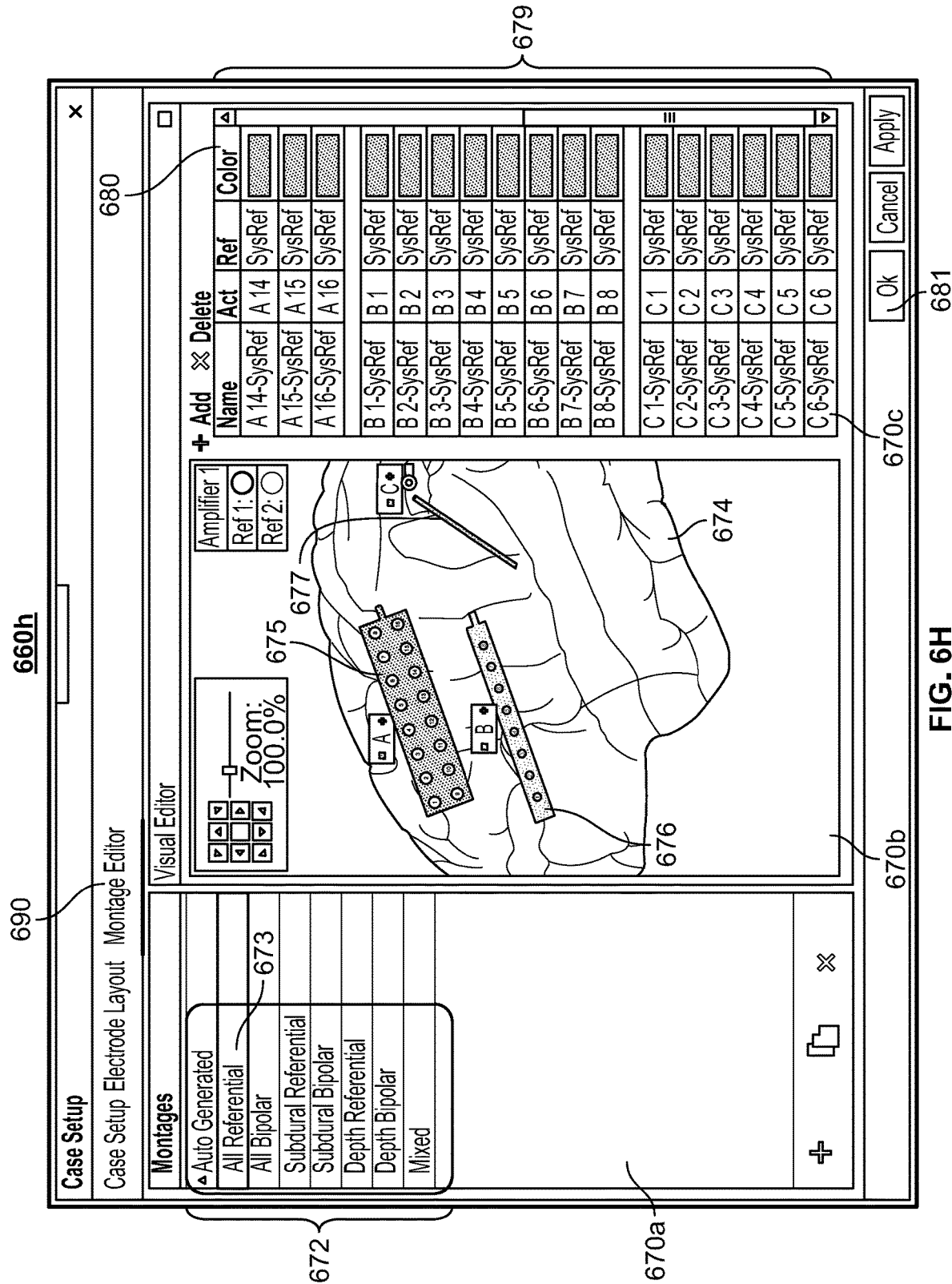
FIG. 6H shows yet another GUI to enable the user to auto-generate referential montages, in accordance with some embodiments of the present specification.

Once the user has configured and added electrodes using the electrode layout tab 689, the user can auto-generate montages. Referring to a GUI 660*h* of FIG. 6H, upon selecting a montage editor tab 690, the user navigates to a first window 670*a* displaying a plurality of montage settings 672 available for auto-generation and a second window 670*b* displaying a view of the patient's brain 674 with positioning of the 8×8 contacts grid electrode 675, the 8 contacts strip electrode 676 and the 10 contacts depth electrode 677. In accordance with an embodiment, when a user selects the 'all referential' setting 673 in the first window 670*a* (and clicks the 'ok' button 681), the module 125 (FIG. 1) automatically creates referential montages 679 for every electrode contact in each of the grid, strip and depth electrodes 675, 676, 677. These auto-generated referential montages 679 are displayed in a third window 670*c* along with their associated color codes 680.

In some embodiments, the module 125 (FIG. 1) allows the user to indicate that the user would like to set up default referential montages for all electrodes or the single electrodes that the user subsequently draws loops around. While setting the default referential montages, the module 125 may allow the user to set a common reference by selecting a reference from a drop down list of references. As a result, either all electrodes are configured automatically as referential montages with respect to the common reference or such referential montages are created only for the electrodes around which the user draws the selection loop.

In some embodiments, the module 125 allows the user to indicate that the user would like to set up default bipolar montages for all electrodes or the pairs of electrodes that the user subsequently draws loops around. As a result, either all electrodes are configured automatically as bipolar montages or such bipolar montages are created only for the pairs of electrodes around which the user draws the selection loop.

In some embodiments, the module 125 allows the user to select one of a plurality of pre-configured bipolar montages that are available to the user from, for example, a drop down list. Such pre-configured bipolar montages may include spatial configurations such as, but not limited to, anterior-posterior bipolar montages, transverse bipolar montages. For subdural grid, strip and depth electrodes additional pre-configured bipolar montages are referred by the terms: Ascending, Descending, Ascending Across, and Descending Across. These terms are applied to the contact numbers or identifications on the electrodes.

Figure 6I:
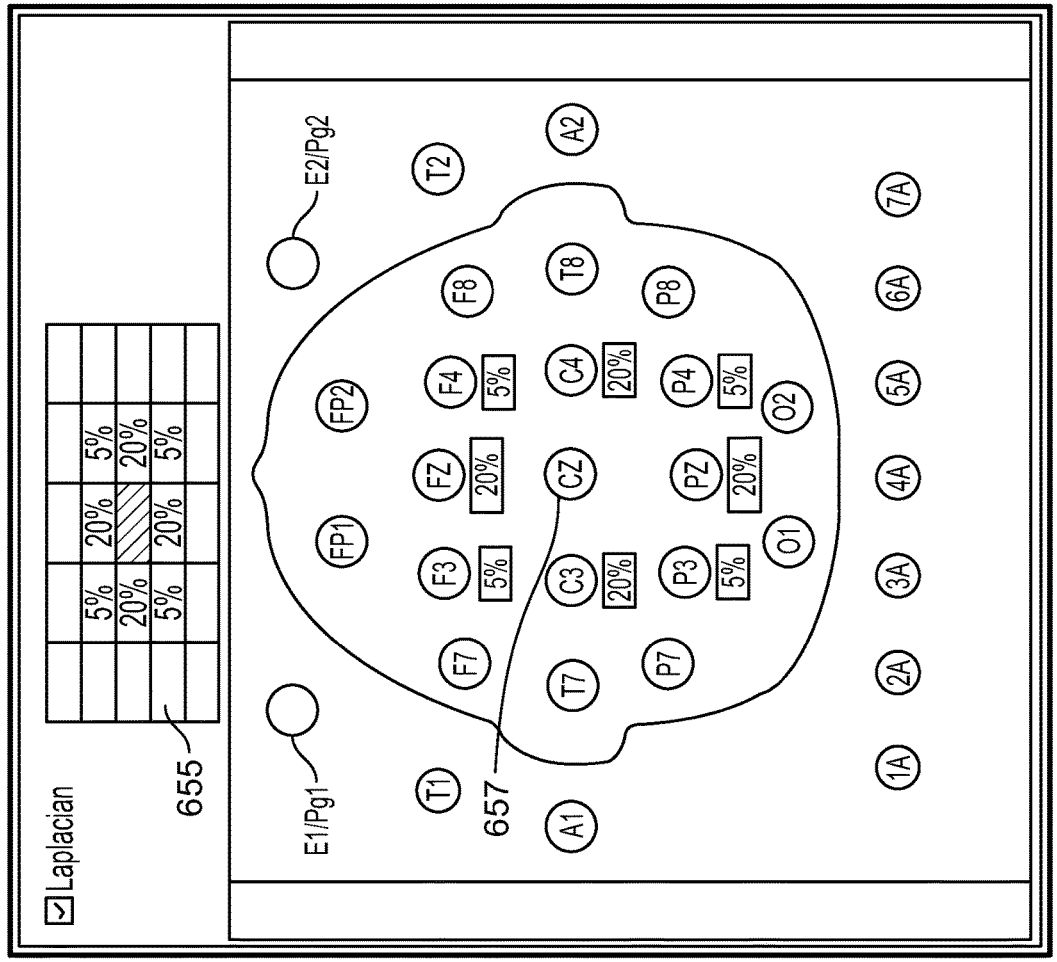
FIG. 6I shows a GUI illustrating generation of a weighted/Laplacian montage, in accordance with some embodiments of the present specification.

In other embodiments, average reference montages are defined by clicking individual electrode contacts or encircling contacts with loops. In some embodiments, when individual electrode contacts are clicked (by the mouse) or encircled (using drawing loops), the module 125 senses such individual electrode contact selections and concludes that the user would either like to create common-reference montages or average reference montages. Accordingly, the module 125 may generate a GUI with options to either create common-reference montages or average reference montages. If the user selects the option of creating common-reference montages, then the dialog box 510 of FIG. 5A is displayed to the user (or the user may follow the method illustrated in FIGS. 6C, 6D and 6E to create common-reference montages). On the other hand, if the user selects the option of creating average reference montages, then recordings from each channel electrode selected by the user are summed up and averaged. In still other embodiments, weighted/Laplacian montages are defined through a weighted pattern applied to electrode contacts proximal to an already selected contact. In some embodiments, selection of the contact, to apply the weighted pattern to, is accomplished by clicking using the mouse. As an illustration, FIG. 6I shows a GUI 635f illustrating a weighted pattern 655 being applied to a plurality of electrode contacts proximal to a selected contact 657 in order to generate a weighted/Laplacian montage.

Figure 7:
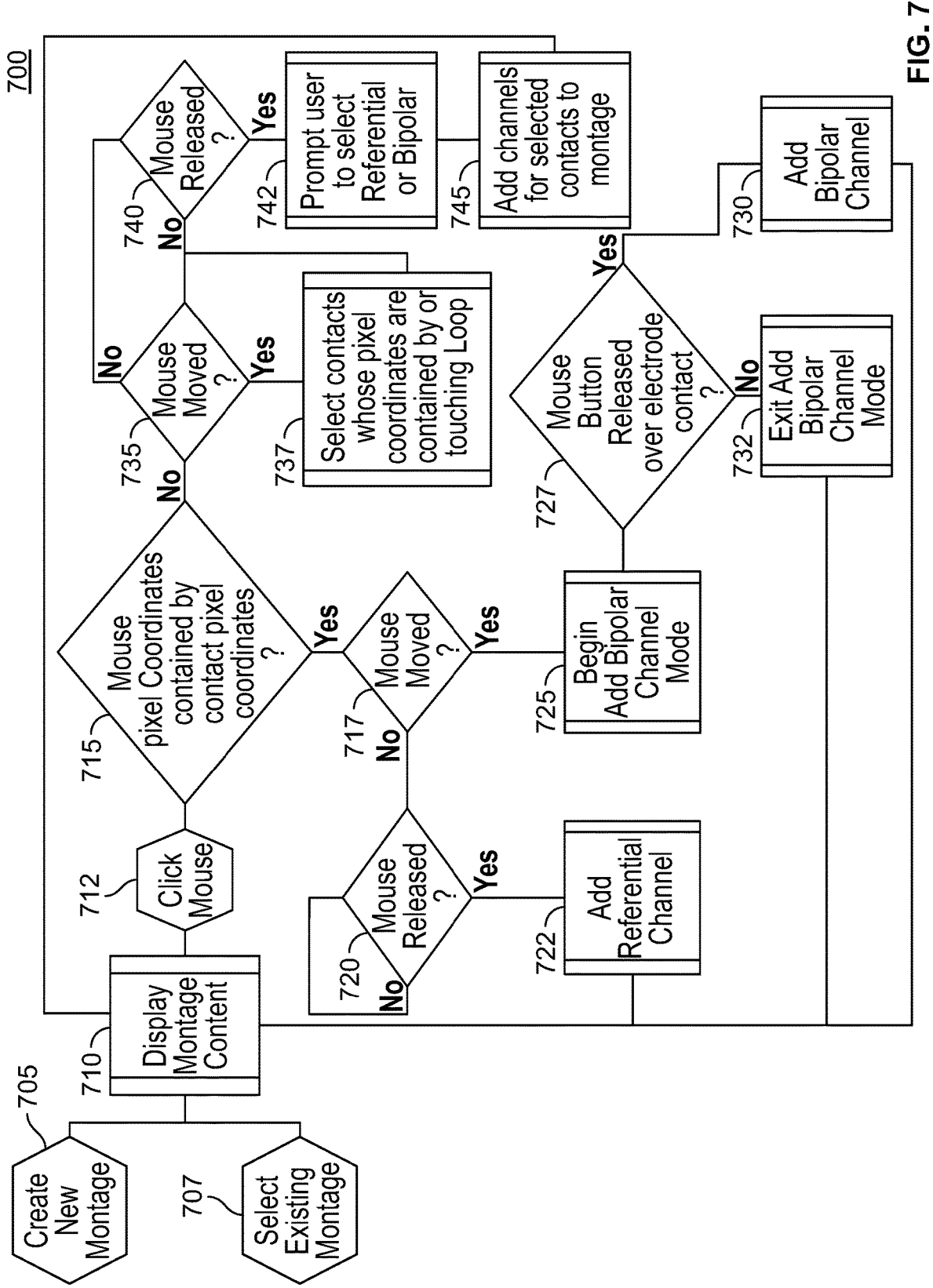
FIG. 7 is a workflow illustrating processes of user-selection and auto-generation of montages using at least one GUI, in accordance with some embodiments of the present specification.

FIG. 7 is a workflow 700 illustrating processes of user-selection and auto-generation of montages using at least one GUI, in accordance with some embodiments of the present specification. The workflow 700 illustrates a plurality of exemplary steps of a first process wherein a user uses a mouse to click on an electrode to add it as a reference montage, a second process wherein the user clicks and drags the mouse pointer between two electrode contacts to create a bipolar montage and a third process wherein the user clicks the mouse in a region that does not display an electrode contact and thereafter drags or moves the mouse pointer to begin drawing a selection loop such that when the mouse is released, all electrode contacts contained in or touched by the drawn loop are automatically added to a montage.

Referring now to FIGS. 1 and 7, to enable the user to create new montage at step 705 and/or to select existing montage at step 707, the automated montage creation module 125 displays 'montage content', at step 710, to the user on at least one GUI. In various embodiments, 'montage content' refers to graphical representation or display of a plurality of electrode contacts associated with a plurality of input channels of at least one amplifier or recording device.

At step 712, the user clicks the mouse pointer or cursor on the GUI. At step 715, the montage creation module 125 determines if the pixel coordinates at the location where the mouse was clicked lies within or is contained by the pixel coordinates associated with a first electrode contact. In other words, it is determined whether the user has clicked on the first electrode contact. If it is determined that the user has clicked the first electrode contact, then at step 717 the module 125 determines if the user has further dragged or moved the mouse pointer. If the mouse was not dragged it is determined if the mouse is released, at step 720. The module 125 awaits the user to release the mouse at step 720. When the mouse is released, signifying that the user has clicked and released the mouse at the first electrode contact, the first electrode contact is added as a referential channel or montage at step 722.

On the other hand, if at step 717, the module 125 determines that the mouse has been moved or dragged (after clicking on the first electrode contact) then, at step 725, the module 125 enters into a bipolar montage addition mode. At step 727, the module 125 determines if the mouse is released on a second electrode contact. If yes, then, at step 730, the first and second electrode contacts are added or used to generate a bipolar montage. If no, that is if the mouse is not released on a second electrode then, at step 732 the module ends or exits from the bipolar montage addition mode.

Referring back to step 715, if it is determined that the user has not clicked on the first electrode contact or any electrode contact at all then, at step 735, the module 125 determines if the mouse has been subsequently dragged or moved. If the mouse has not been dragged or moved then the process flow moves to step 740. However, if the mouse has been dragged or moved this signifies that the user is using a drawing loop to encircle one or more electrode contacts. Consequently, at step 737, the module 125 selects all electrode contacts whose pixel coordinates are contained within or touched by the coordinates of the drawing loop. Next, at step 740, the module 125 awaits for the user to release the mouse. If the mouse is not released, the process flow moves back to step 735. However, on release of the mouse, the user is prompted, at step 742, to select whether the encircled one or more electrode contacts should be used to generate bipolar or referential montage. At step 745, the channels corresponding to the encircled one or more electrode contacts are added to bipolar or referential montage based on user choice at step 742.

In various embodiments, the systems and methods of the present specification enable a user to create and select montages in manners which simplify operational workflow, reduce the risk of errors, and reduce setup and surgical time compared to current systems. In addition, the systems and methods of the present specification enhance data accuracy and analyses to improve patient outcomes.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A computer readable non-transitory medium comprising a plurality of executable programmatic instructions wherein, when the plurality of executable programmatic instructions are executed by a processor in a computing device, at least one user-defined montage from a plurality of EEG electrodes positioned in a patient's brain, on the patient's brain or on the patient's scalp is generated, the plurality of executable programmatic instructions comprising:

programmatic instructions, stored in the computer readable non-transitory medium, for generating a first graphical interface to display at least one graphical view of the patient's brain and/or scalp overlaid with a plurality of identifications corresponding to the plurality of EEG electrodes, wherein each of the plurality of identifications uniquely references a position of each of the plurality of EEG electrodes relative to the patient's brain and/or scalp;

programmatic instructions, stored in the computer readable non-transitory medium, for displaying a tool within the first graphical interface, wherein the tool is configured to be manipulated in order to select at least one identification of the plurality of identifications;

programmatic instructions, stored in the computer readable non-transitory medium, for prompting a user to indicate at least one reference identification corresponding to the at least one identification, wherein, when executed, the programmatic instructions configured to enable the user select at least one identification:

enables the user to use at least two drawing loops to select electrodes for generating a first montage and a second montage;

upon forming the at least two drawing loops, automatically generates a second graphical interface to prompt the user to identify at least one of active electrode(s) or reference electrode(s) of the electrodes enclosed by each of the at least two drawing loops; and upon identifying the active electrode(s) or the reference electrode(s), automatically designates the other electrode(s);

programmatic instructions, stored in the computer readable non-transitory medium, for acquiring EEG signals associated with the EEG electrodes corresponding to the at least one identification and the at least one reference identification; and programmatic instructions, stored in the computer readable non-transitory medium, for generating a third graphical interface to display at least one EEG trace indicative of the EEG signals associated with the EEG electrodes corresponding to the at least one identification and the at least one reference identification.

2. The computer readable non-transitory medium of claim 1, further comprising programmatic instructions configured to enable the user to input a selection of the at least one identification comprising at least one of programmatic instructions programmatic instructions for enabling a clicking from the at least one identification to multiple other identifications of the plurality of identifications to thereby visually connect the at least one identifications and multiple other identifications, programmatic instructions for enabling at least one of clicking or dragging an icon over or looping around at least one of the plurality of EEG electrodes, programmatic instructions for enabling a clicking a body of at least one of the plurality of EEG electrodes or programmatic instructions for enabling a pressing a key on a keyboard and clicking upon more than one of the plurality of EEG electrodes.

3. The computer readable non-transitory medium of claim 1, further comprising programmatic instructions configured to prompt the user to indicate at least one of a first identification and a second identifications as the at least one reference identification, wherein the at least one identification comprises the first identification and the second identification.

4. The computer readable non-transitory medium of claim 1, wherein said plurality of EEG electrodes comprises at least one of strip, grid or depth electrodes.

5. The computer readable non-transitory medium of claim 1, further comprising programmatic instructions for acquiring the EEG signals in real time while said EEG signals are being recorded using the plurality of EEG electrodes.

6. The computer readable non-transitory medium of claim 1, further comprising programmatic instructions configured to acquire the EEG signals from a database system, wherein the database system is configured to store the EEG signals for offline processing.

7. The computer readable non-transitory medium of claim 1, wherein the at least one identification is a single identification.

8. The computer readable non-transitory medium of claim 7, further comprising programmatic instructions configured to further prompt the user to indicate the at least one reference identification from said plurality of identifications, and wherein said at least one reference identification is same for any subsequently selected single identifications.

9. A computer-implemented method of enabling a generation of at least one user-defined montage from a plurality of EEG electrodes positioned in a patient's brain, on the patient's brain and/or on the patient's scalp, said method comprising:

generating a first graphical interface to visually display at least one view of the patient's brain and/or scalp overlaid with a spatial distribution of the plurality of EEG electrodes, wherein each of said plurality of EEG electrodes in the at least one view is uniquely identified with reference to its position in the patient's brain, on the patient's brain and/or on the patient's scalp;

displaying a tool within the first graphical interface;

receiving an input from a user using the tool to select at least one electrode from the plurality of EEG electrodes displayed in the at least one view;

prompting the user to indicate at least one reference electrode corresponding to the selected at least one electrode wherein using the tool to select the at least one electrode comprises:

allowing the user to use at least two drawing loops to select electrodes corresponding to a first montage and electrodes corresponding to a second montage;

upon forming the at least two drawing loops, generating a second graphical interface to prompt the user to identify the at least one electrode and the at least one reference electrode from the electrodes enclosed by each of the at least two drawing loops; and upon identifying the at least one electrode or the at least one reference electrode, automatically designating the other electrode(s);

accessing EEG signals corresponding to the at least one electrode and the at least one reference electrode; and generating a third graphical interface to display at least one EEG trace indicative of a comparison of EEG signals of the at least one electrode and the at least one reference electrode.

10. The computer-implemented method of claim 9, wherein selecting the at least one electrode from the plurality of EEG electrodes further comprises at least one of clicking on multiple electrodes of the plurality of EEG electrodes to visually connect them, clicking or dragging an icon over or looping the at least one electrode, clicking a body of the at least one electrode, or by pressing a key on a keyboard and clicking upon at least one electrode and additional electrodes of the plurality of EEG electrodes.

11. The computer-implemented method of claim 9, further comprising receiving a selection of the at least one electrode and a second electrode from the plurality of EEG electrodes in the at least one view, wherein the at least one electrode and the second electrode are adjacent to each other.

12. The computer-implemented method of claim 11, further comprising further prompting the user to indicate one of the at least one electrode and the second electrode as the at least one reference electrode.

13. The computer-implemented method of claim 9, wherein said plurality of EEG electrodes comprises at least one of strip, grid or depth electrodes.

14. The computer-implemented method of claim 9, further comprising acquiring the EEG signals in real time while the EEG signals are being recorded using said plurality of EEG electrodes.

15. The computer-implemented method of claim 9, further comprising acquiring the EEG signals from a database system configured to store the EEG signals for offline processing.

16. The computer-implemented method of claim 9, further comprising receiving a selection of only the at least one electrode in the at least one view.

17. The computer-implemented method of claim 16, further comprising further prompting the user to indicate the at least one reference electrode from the plurality of electrodes, wherein the at least one reference electrode is designated to be a same reference electrode for any subsequently selected electrodes from the plurality of electrodes.

18. A computer-implemented method of enabling a real-time generation of at least one user-defined bipolar montage from a plurality of EEG electrodes positioned in a patient's brain, on the patient's brain and/or on the patient's scalp, said method comprising:

generating a first graphical interface to display at least one view of said patient's brain and/or scalp overlaid with a plurality of identifications corresponding to the plurality of EEG electrodes, wherein each of said identifications uniquely references each of the plurality of EEG electrodes in the patient's brain, on the patient's brain and/or on the patient's scalp;

displaying a tool within the first graphical interface, wherein the tool is configured to receive a user's input that selects a first identification and a second identification;

prompting the user to indicate a reference identification from the selected first identification and the second identification, wherein using the tool to select the first identification and the second identification comprises a) enabling the user to use a first drawing loop to select the first identification and the second identification for generating a montage, b) upon forming the drawing loop, generating a second graphical interface to prompt the user to identify the active electrode or reference electrode of the first identification and the second identification enclosed by the drawing loop, and c) upon identifying the active electrode or the reference electrode, automatically designating the other electrode;

acquiring EEG signals associated with the plurality of EEG electrodes corresponding to the first identification and the second identification; and generating a third graphical interface to display an EEG trace associated with the first identification, the second identifications and the reference identification, wherein the plurality of EEG electrodes include at least one of strip, grid or depth electrodes.

19. The computer-implemented method of claim 18, wherein selecting the first identification and the second identification further comprises at least one of clicking on the first identification and the second identification to visually connect them, clicking and dragging an icon over or looping the first identification and the second identification, clicking a body of the first identification and the second identification, or by pressing a key on a keyboard and clicking upon the first identification and the second identification.

20. The computer-implemented method of claim 18, further comprising acquiring the EEG signals in real time while the EEG signals are being recorded using the plurality of EEG electrodes.

21. The computer-implemented method of claim 18, further comprising acquiring the EEG signals from a database system configured to store the EEG signals for offline processing.

* * * * *